(12) United States Patent
Takayama et al.

(10) Patent No.: US 7,109,208 B2
(45) Date of Patent: Sep. 19, 2006

(54) VISUAL FUNCTION DISORDER IMPROVING AGENTS

(75) Inventors: Yoshiko Takayama, Kobe (JP); Yukuo Yoshida, Kobe (JP); Masayoshi Uehata, Tokyo (JP)

(73) Assignees: Senju Pharmaceutical Co., Ltd., Osaka (JP); Mitsubishi Pharma Corporation, Osaka (JP)

( * ) Notice: Subject to any disclaimer, the term of this patent is extended or adjusted under 35 U.S.C. 154(b) by 0 days.

(21) Appl. No.: 10/474,369

(22) PCT Filed: Apr. 11, 2002

(86) PCT No.: PCT/JP02/03590

§ 371 (c)(1),
(2), (4) Date: Nov. 18, 2003

(87) PCT Pub. No.: WO02/083175

PCT Pub. Date: Oct. 24, 2002

(65) Prior Publication Data

US 2004/0106646 A1    Jun. 3, 2004

(30) Foreign Application Priority Data

Apr. 11, 2001  (JP)  .............. 2001-113329
Oct. 3, 2001   (JP)  .............. 2001-308010

(51) Int. Cl.
  *A61K 31/437*  (2006.01)
  *A61K 31/44*   (2006.01)
(52) U.S. Cl. ............ 514/300; 514/352; 514/343; 514/332; 514/329; 514/326
(58) Field of Classification Search ......... 514/300, 514/326, 329, 332, 343, 352
See application file for complete search history.

(56) References Cited

U.S. PATENT DOCUMENTS

| | | | |
|---|---|---|---|
| 4,456,757 A | 6/1984 | Hidaka et al. | |
| 4,678,783 A | 7/1987 | Hidaka et al. | |
| 5,478,838 A | 12/1995 | Arita et al. | |
| 5,733,904 A | 3/1998 | Fujii et al. | |
| 5,747,507 A | 5/1998 | Ikegaki et al. | |
| 5,906,819 A | 5/1999 | Kaibuchi et al. | |
| 5,958,944 A | 9/1999 | Arita et al. | |
| 6,153,608 A | 11/2000 | Hidaka et al. | |
| 6,156,766 A | 12/2000 | Arita et al. | |
| 6,218,410 B1 | 4/2001 | Uehata et al. | |
| 6,329,547 B1 | 12/2001 | Shirasawa et al. | |
| 6,673,812 B1 * | 1/2004 | Azuma et al. | 514/303 |
| 2002/0032148 A1 | 3/2002 | Uehata et al. | |
| 2003/0158413 A1 | 8/2003 | Takanashi et al. | |

FOREIGN PATENT DOCUMENTS

| EP | 728480 | 8/1986 |
|---|---|---|
| EP | 0 609 822 | 8/1994 |
| EP | 609822 | 8/1994 |
| EP | 0 728 480 | 8/1996 |
| EP | 1 034 793 | 9/2000 |
| EP | 1034793 | 9/2000 |
| EP | 1 064 944 | 1/2001 |
| EP | 1064944 | 1/2001 |
| EP | 1 256 574 | 11/2002 |
| JP | 62-89679 | 4/1987 |
| JP | 2-256617 | 10/1990 |
| JP | 3/218356 | 9/1991 |
| JP | 4-264030 | 9/1992 |
| JP | 4-273821 | 9/1992 |
| JP | 6-041080 | 2/1994 |
| JP | 6-293643 | 10/1994 |
| JP | 7-041424 | 2/1995 |
| JP | 7-277979 | 10/1995 |
| JP | 9-227381 | 9/1997 |
| JP | 10-087491 | 4/1998 |
| JP | 10-113187 | 5/1998 |
| JP | 10-201 480 | 8/1998 |
| JP | 10 201 480 | 8/1998 |
| JP | 10-201480 | 8/1998 |
| JP | 2001-08 1048 | 3/2001 |
| JP | 2001-81048 | 3/2001 |
| WO | 94/05290 | 3/1994 |
| WO | 97/19694 | 6/1997 |
| WO | 97/23222 | 7/1997 |
| WO | 98/06433 | 2/1998 |
| WO | 98/34485 | 8/1998 |
| WO | 99/00133 | 1/1999 |
| WO | 99/23113 | 5/1999 |
| WO | 00/57914 | 10/2000 |

OTHER PUBLICATIONS

Hirose, Masaya et al., "Molecular Dissection of the Rho-associated Protein Kinase (p160ROCK)-regulated Neurite Remolding in Neuroblastoma N1E-115 Cells", The Journal of Cell Biology, vol. 141, No. 7, Jun. 29, 1998, pp. 1625-1636.

Lehmann, Maxine et al., "Inactivation of Rho Signaling Pathway CNS Axon Regeneration", Journal of Neuroscience, vol. 19, No. 17, Sep. 1, 1999, pp. 7537-7547.

(Continued)

*Primary Examiner*—Charanjit S. Aulakh
(74) *Attorney, Agent, or Firm*—Wenderoth, Lind & Ponack, L.L.P.

(57) ABSTRACT

The present invention provides a visual function disorder improving agent containing a compound having Rho kinase inhibitory activity, particularly (R)-(+)-N-(1H-pyrrolo[2,3-b]pyridin-4-yl)-4-(1-aminoethyl)benzamide, as an effective component. This agent has axon of the retinal ganglion cellal extension promoting action and optic nerve cell regeneration promoting action, and is useful for the treatment of a visual function disorder associated with various eye diseases caused by damage, defects, degeneration and the like in the retinal or optic nerve.

8 Claims, 5 Drawing Sheets

OTHER PUBLICATIONS

Bito, Haruhiko et al., "A Critical Role for a Rho-Associated Kinase, p160ROCK, in Determining Axon Outgrowth in Mammalian CNS Neurons", Neuron, vol. 26, May 2000, pp. 431-441.

Bulletin of the Japanese Society for Neurochimistry, vol. 40, Nos. 2 and 3, 2001, p. 253 (S47-6).

Naunyn-Schmiedeberg's Archives of Pharmacology, Supplement to vol. 358, No. 1, 1998, p. R219.

Hirose, M. et al., "Molecular Dissection of the Rho-associated Protein Kinase (160ROCK)-regulated Neurite Remodeling in Neuroblastoma N1E-115 Cells.", J. Cell. Biol., 1998, 141 (7), pp. 1625-1636.

Lehamann, M., et al., "Inactivation of Rho Signaling Pathway Promotes CNS Axon Regeneration". J. Neurosci., 1999, 19 (17), pp. 7537-7547.

Bito, H., et al., "A critical role for a Rho-associated kinase, p160ROCK, in determining axon outgrowth in mammaliman CNS neurons." Neuron, 2000, 26(2), pp. 431-441.

McKerracher, L. "Strategies to promote regeneration of adult rat renal ganglion cell axons in the nerve." Bullet of the Japanese Society for Neurochemistry, 2001 4 (2/3), pp. 253 (S47-6).

* cited by examiner

A : FCS (+), Compound 2 (−)
B : FCS (−), Compound 2 (−)
C : FCS (−), Compound 2 (+)
D : FCS (−), Compound 2 (−), LPA (+)

Normal group

Control group

Compound 2
treatment group-1

VISUAL FUNCTION DISORDER IMPROVING AGENTS

This application is a U.S. National Stage of International Application No. PCT/JPO2/03590 filed Apr. 11, 2002.

TECHNICAL FIELD

The present invention relates to a visual function disorder improving agent containing a compound having Rho kinase inhibitory activity.

BACKGROUND OF THE INVENTION

The retinal ganglion cell is a retinal output cell, and its axon is also called an optic nerve fibers, runs in the retinal inner layer and the nerve fibers layer (nearest side to the vitreous body), gathers at the optic disc, leaves the eye ball, forms an optic nerve and undertakes a role of transmitting visual information to the cerebral cortex. Moreover, the retinal ganglion cell is distributed over the entire area of the retina. Accordingly, for example, a retinal damage due to inflammation and the like causes retinal neuropathy, retinal vascular occlusion, periphlebitis retinae, Eales' disease, ischemic ophthalmopathy, retinal arteriolar microaneurysm, retinopathy caused by hypertension, renal disease and blood disease, diabetic retinopathy, retinal dystrophy, macular dystrophy, chorioretinopathy, macular degeneration, macular edema, retinal pigment epithelium detachment, degenerative retinoschisis, retinoblastoma, retinal pigment epithelioma and the like, along with which a visual disorder occurs. Furthermore, degeneration and damage of the optic nerve causes the onset of optic neuritis, capillary angioma of optic disc, ischemic optic neuropathy, defects of retinal nerve fibers layer, retinal optic atrophy, neurotmesis of optic nerve, traumatic optic neuropathy, choked disc, coloboma of optic disc, optic nerve hypoplasia, toxic optic atrophy and the like, along with which a visual disorder occurs. It is further known that elevated intraocular pressure (glaucoma etc.) and the like cause atrophy and degeneration of the optic nerve, which in turn causes a visual disorder. For these visual disorders, a pharmaceutical agent capable of recovering the function of the visual information transmission pathway in the retina, particularly a pharmaceutical agent capable of neogenesis (regeneration) of the axon of retinal ganglion cell and promotion of extension thereof, and a pharmaceutical agent capable of neogenesis (regeneration) of the optic nerve cell are considered to be useful. While surgical efforts have been made in recent years such as retinal transplantation and retinal regeneration, in such efforts, too, it is highly useful to find a means and a pharmaceutical agent to promote neogenesis (regeneration) and extension of the optic nerve axon after transplantation.

On the other hand, as a compound having a Rho kinase inhibitory activity, a compound of the formula (I) to be mentioned later has been reported recently [WO98/06433 (corresponding patents: EP956865 and U.S. Pat. No. 6,218, 410)]. Certain isoquinolinesulfonamide derivative and isoquinoline derivative are also reported to show a Rho kinase inhibitory activity (WO98/06433 and Naunyn-Schmiedeberg's Archives of Pharmacology 385(1) Suppl., R219, 1998). Furthermore, it has been reported that ethacrynic acid, certain vinyl benzene derivatives such as 4-[2-(2,3,4, 5,6-pentafluorophenyl)-acryloyl]cinnamic acid and the like have a Rho kinase inhibitory activity [WO00/57914, JP-A-2000-44513 (corresponding patents: EP1094055 and U.S. Pat. No. 6,329,547)]. In addition, it has been reported that certain kinds of nitrogen-containing compounds, inclusive of N-[1-(3,5-dimethoxybenzyl)-tetrahydro-1H-3-pyrrolyl]-N-(1H-5-indazolyl)amine, have Rho kinase inhibitory activity (WO01/56988). It has been also reported that certain kinds of thiochroman compounds have Rho kinase inhibitory activity (WO01/68607).

The Rho kinase is a serin/threonine kinase activated along with the activation of Rho, and is known to function at the downstream of Rho and phosphorylate various substances, thereby controlling various physiological functions such as formation of stress fibers and desmosomes, contraction of smooth muscle, retraction of nerve axon and the like.

Inhibition of Rho kinase having such various physiological functions is considered to lead to the prophylaxis or treatment of various disease states, diseases and disorders. For example, as a pharmaceutical use of a compound having Rho kinase inhibitory activity, WO98/06433 widely discloses a therapeutic agent of hypertension, a therapeutic agent of angina pectoris, a cerebrovascular spasm suppressant, a therapeutic agent of asthma, a therapeutic agent of peripheral circulatory disturbance, a premature delivery preventive, a therapeutic agent of arterial sclerosis, an anticancer drug, an anti-inflammatory agent, an immunosuppressant, a therapeutic agent of autoimmune diseases, an anti-AIDS agent, a therapeutic agent of osteoporosis, a therapeutic agent of retinopathy, a cerebral function improver, a contraceptive drug, and a gastrointestinal tract infection preventive. In addition, WO01/56988 published after the earliest priority date of the present application describes that a specific compound having Rho kinase inhibitory activity is useful as a therapeutic agent of hypertension, asthma, angina pectoris, cerebrovascular contraction, peripheral circulation disorder, threatened abortion, glaucoma, tunnel vision, frequent urination, cancer, infiltration and metastasis of cancer, arteriosclerosis, retinopathy, immune response, inflammatory autoimmune disease, cerebral function disorder, osteoporosis, bacterial infection, chronic kidney failure, chronic nephritis, diabetic nephropathy, IgA nephropathy, a disease relating to the formation of thrombus, rheumatism, erectile dysfunction and fibrosis. Since it also has intraocular pressure lowering action, optic disc blood flow increasing action and aqueous humor outflow promoting action based on cilliary muscle relaxing action, its use as an agent for the prophylaxis or therapy of glaucoma has been reported [WO00/09162 (corresponding to EP1034793)]. WO00/57914 also describes its usefulness as an intraocular pressure lowering agent.

Furthermore, the compound of formula (I) has been already known to be useful as an agent for the prophylaxis or treatment of disorders of circulatory organs such as coronary, cerebral, renal, peripheral artery and the like (e.g., a therapeutic agent of hypertension, a therapeutic agent of angina pectoris, a therapeutic agent of renal and peripheral circulation disorder, a suppressive agent of cerebrovascular contraction and the like), which is potent and long lasting, and also as a therapeutic agent of asthma [JP-A-62-89679, JP-A-3-218356, JP-A-4-273821, JP-A-5-194401 (corresponding patents; EP641781 and U.S. Pat. No. 5,478,838), JP-A-6-41080 and WO95/28387 (corresponding patents; EP757038, U.S. Pat. No. 5,958,944 and U.S. Pat. No. 6,156,766)].

The isoquinolinesulfonamide derivative described in the above-mentioned WO98/06433 is known to be effective as a vasodilating agent, a therapeutic agent of hypertension, a cerebral function improver, an anti-asthma agent, a heart protecting agent, a platelet aggregation inhibitor, a therapeutic agent of neurologic manifestation, an anti-inflammatory agent, an agent for the prevention and treatment of hyperviscosity syndrome, a therapeutic agent of glaucoma, an intraocular pressure lowering agent, an improver of motor paralysis due to of cerebral thrombosis, an agent for prevention and treatment of virus infection and transcriptional control factor inhibitor [JP-A-57-200366, JP-A-61-227581, JP-A-2-256617, JP-A-4-264030, JP-A-6-56668 (corresponding patents; EP654266 and U.S. Pat. No. 5,747,507), JP-A-6-80569 (corresponding patent; WO94/05290), JP-A-6-293643, JP-A-7-41424, JP-A-7-277979, WO97/23222 (corresponding patents; EP868186 and U.S. Pat. No. 6,271,224), JP-A-9-227381, JP-A-10-45598 and JP-A-10-87491].

Moreover, the isoquinoline derivative described in the above-mentioned publication (Naunyn-Schmiedeberg's Archives of Pharmacology 385(1) Suppl., R219, 1998) is known to be useful as an agent for the prevention and treatment of brain tissue disorder due to vasospasm [WO97/28130 (corresponding patents; EP885888 and U.S. Pat. No. 6,153,608)].

However, there is no description disclosing that a compound having Rho kinase inhibitory activity has an action to improve visual function disorder or an action to improve visual function disorder caused by damage and/or degeneration of retinal nerve cell (the neural retina) or optic nerve (the nervus opticus), particularly an action to promote regeneration and extension of the axon of retinal ganglion cell.

The Rho-Rho kinase pathway is known to exhibit various functions in living organism as mentioned above, and involvement in the extension of nerve axon has been recently reported (The Journal of Cell Biology, vol. 141, 1625–1636 (1998), Neuron, 26, 431–441 (2000), The Journal of Neuroscience, vol. 19(17), 7537–7547 (1999)). However, none of them directly teaches the role of Rho kinase in retinal ganglion cell or the effect afforded by a Rho kinase inhibitor, and there is no description to suggest the usefulness of the Rho kinase inhibitor in the recovery of the visual function.

DISCLOSURE OF THE INVENTION

An object of the present invention is to provide a novel visual function disorder improving agent useful for recovery of the visual function impaired due to damage and/or degeneration of the retinal nerve cell or optic nerve. The present invention aims at provision of a pharmaceutical agent useful for neogenesis, extension and promotion of extension of the axon of a retinal ganglion cell, as well as regeneration of an optic nerve cell.

The present inventors have conducted intensive studies in an attempt to solve the above-mentioned problems and found that a compound having Rho kinase inhibitory activity has an action of neogenesis, extension and promotion of extension of axon of a retinal ganglion cell, as well as an optic nerve cell regenerating action, and therefore found that the compound is useful for the recovery of the visual function impaired due to damage and/or degeneration of the retinal nerve cell or optic nerve, which resulted in the completion of the present invention.

Accordingly, the present invention provides the following.

(1) A visual function disorder improving agent that improves a visual function disorder caused by damage or degeneration of retinal nerve cell or optic nerve, which contains a compound having Rho kinase inhibitory activity.

(2) The visual function disorder improving agent of the above-mentioned (1), wherein the improvement of the visual function disorder is by way of promotion of extension of axon of a retinal ganglion cell.

(3) The visual function disorder improving agent of the above-mentioned (1), wherein the improvement of the visual function disorder is by way of regeneration of the optic nerve cell.

(4) An agent for promoting extension of axon of a retinal ganglion cell, which comprises a compound having Rho kinase inhibitory activity as an effective component.

(5) An agent for promoting regeneration of an optic nerve cell, which comprises a compound having Rho kinase inhibitory activity as an effective component.

(6) The agent of any of (1) to (5) above, wherein the compound having a Rho kinase inhibitory activity is an amide compound of the following formula (I)

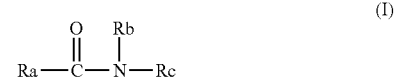

wherein
Ra is a group of the formula

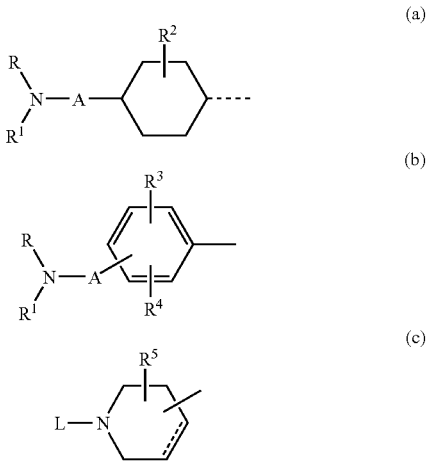

in the formulas (a) and (b),
R is hydrogen, alkyl, or cycloalkyl, cycloalkylalkyl, phenyl or aralkyl, which optionally has a substituent on the ring, or a group of the formula

wherein $R^6$ is hydrogen, alkyl or formula: —$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom,
$R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or di-alkylcarbamoyl or azide, and A is a group of the formula

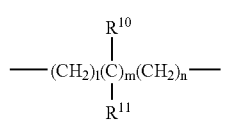
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, in the formula (c), L is hydrogen, alkyl, aminoalkyl, mono- or dialkylaminoalkyl, tetrahydrofurfuryl, carbamoylalkyl, phthalimidoalkyl, amidino or a group of the formula

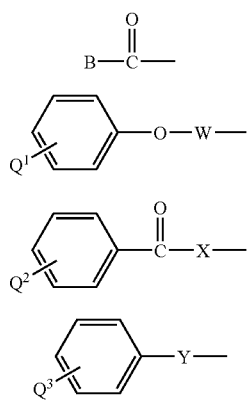
(f)
(g)
(h)
(i)

wherein B is hydrogen, alkyl, alkoxy, aralkyl, aralkyloxy, aminoalkyl, hydroxyalkyl, alkanoyloxyalkyl, alkoxycarbonylalkyl, α-aminobenzyl, furyl, pyridyl, phenyl, phenylamino, styryl or imidazopyridyl, $Q^1$ is hydrogen, halogen, hydroxy, aralkyloxy or thienylmethyl, W is alkylene, $Q^2$ is hydrogen, halogen, hydroxy or aralkyloxy, X is alkylene, $Q^3$ is hydrogen, halogen, hydroxy, alkoxy, nitro, amino, 2,3-dihydrofuryl or 5-methyl-3-oxo-2,3,4,5-tetrahydropyridazin-6-yl; and Y is a single bond, alkylene or alkenylene, and in the formula (c), a bond denoted by a broken line and a solid line is a single bond or a double bond;

$R^5$ is hydrogen, hydroxy, alkoxy, alkoxycarbonyloxy, alkanoyloxy or aralkyloxycarbonyloxy;

Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof, or a prodrug thereof.

(7) The agent of any of (1) to (5) above, wherein the compound having a Rho kinase inhibitory activity is an amide compound of the following formula (I')

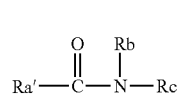
(I')

wherein

Ra' is a group of the formula

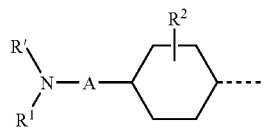
(a')

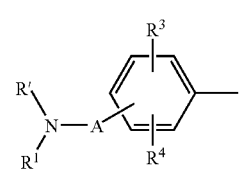
(b')

wherein

R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^2$ is hydrogen or alkyl, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

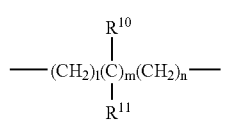
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and l, m and n are each 0 or an integer of 1–3, Rb is a hydrogen, an alkyl, an aralkyl, an aminoalkyl or a mono- or dialkylaminoalkyl; and Rc is an optionally substituted heterocycle containing nitrogen, an isomer thereof and/or a pharmaceutically acceptable acid addition salt thereof, or a prodrug thereof.

(8) The agent of any of (1) to (5) above, wherein the compound having a Rho kinase inhibitory activity is (R)-(+)-N-(1H-pyrrolo[2,3-b]pyridin-4-yl)-4-(1-aminoethyl)benzamide, and/or a pharmaceutically acceptable acid addition salt thereof, or a prodrug thereof, especially (R)-(+)-N-(1H-pyrrolo[2,3-b]pyridin-4-yl)-4-(1-aminoethyl)benzamide monohydrochloride.

(9) The agent of any of (1) to (5) above, wherein the compound having Rho kinase inhibitory activity is a compound selected from thiochroman compounds, isoquinolinesulfonamide derivatives, vinylbenzene derivatives and ethacrynic acid or a pharmaceutically acceptable salt thereof.

(10) A pharmaceutical composition for improving a visual function disorder, which comprises a compound having Rho kinase inhibitory activity and a carrier acceptable for formulation of a preparation, which improves a visual function disorder caused by damage or degeneration of retinal nerve cell or optic nerve.

(11) The pharmaceutical composition for improving visual function disorder of the above-mentioned (10), wherein the improvement of the visual function disorder is by way of promotion of extension of axon of a retinal ganglion cell.

(12) The pharmaceutical composition for improving visual function disorder of the above-mentioned (10), wherein the improvement of the visual function disorder is by way of regeneration of an optic nerve cell.

(13) A pharmaceutical composition for promoting extension of axon of a retinal ganglion cell, which comprises a compound having Rho kinase inhibitory activity and a carrier acceptable for formulation of a preparation.

(14) A pharmaceutical composition for promoting regeneration of an optic nerve cell, which comprises a compound having Rho kinase inhibitory activity and a carrier acceptable for formulation of a preparation.

(15) The pharmaceutical composition of any of the above-mentioned (10)–(14), wherein the compound having Rho kinase inhibitory activity is an amide compound represented by the above-mentioned formula (I), an isomer thereof and/or a pharmaceutically acceptable acid addition salt thereof, or a prodrug thereof.

(16) The pharmaceutical composition of any of the above-mentioned (10)–(14), wherein the compound having Rho kinase inhibitory activity is an amide compound represented by the above-mentioned formula (I'), an isomer thereof and/or a pharmaceutically acceptable acid addition salt thereof, or a prodrug thereof.

(17) The pharmaceutical composition of any of the above-mentioned (10)–(14), wherein the compound having Rho kinase inhibitory activity is (R)-(+)-N-(1H-pyrrolo[2,3-b]pyridin-4-yl)-4-(1-aminoethyl)benzamide or a pharmaceutically acceptable acid addition salt thereof, or a prodrug thereof, particularly (R)-(+)-N-(1H-pyrrolo[2,3-b]pyridin-4-yl)-4-(1-aminoethyl)benzamide monohydrochloride.

(18) The pharmaceutical composition of any of the above-mentioned (10)–(14), wherein the compound having Rho kinase inhibitory activity is a compound selected from thiochroman compounds, isoquinolinesulfonamide derivatives, vinylbenzene derivatives and ethacrynic acid or a pharmaceutically acceptable salt thereof.

(19) A method of improving a visual function disorder caused by damage or degeneration of a retinal nerve cell or anoptic nerve, which comprises administering an effective amount of a compound having Rho kinase inhibitory activity to a patient.

(20) The method of the above-mentioned (19), wherein the improvement of the visual function disorder is by way of promotion of extension of axon of a retinal ganglion cell.

(21) The method of the above-mentioned (19), wherein the improvement of the visual function disorder is by way of regeneration of an optic nerve cell.

(22) A method of promoting extension of axon of a retinal ganglion cell, which comprises administering an effective amount of a compound having Rho kinase inhibitory activity to a patient.

(23) A method of promoting regeneration of an optic nerve cell, which comprises administering an effective amount of a compound having Rho kinase inhibitory activity to a patient.

(24) The method of any of the above-mentioned (19)–(23), wherein the compound having Rho kinase inhibitory activity is an amide compound represented by the above-mentioned formula (I), an isomer thereof and/or a pharmaceutically acceptable acid addition salt thereof, or a prodrug thereof.

(25) The method of any of the above-mentioned (19)–(23), wherein the compound having Rho kinase inhibitory activity is an amide compound represented by the above-mentioned formula (I'), an isomer thereof and/or a pharmaceutically acceptable acid addition salt thereof, or a prodrug thereof.

(26) The method of any of the above-mentioned (19)–(23), wherein the compound having Rho kinase inhibitory activity is (R)-(+)-N-(1H-pyrrolo[2,3-b]pyridin-4-yl)-4-(1-aminoethyl)benzamide or a pharmaceutically acceptable acid addition salt thereof, or a prodrug thereof, particularly (R)-(+)-N-(1H-pyrrolo[2,3-b]pyridin-4-yl)-4-(1-aminoethyl)benzamide monohydrochloride.

(27) The method of any of the above-mentioned (19)–(23), wherein the compound having Rho kinase inhibitory activity is a compound selected from thiochroman compounds, isoquinolinesulfonamide derivatives, vinylbenzene derivatives and ethacrynic acid or a pharmaceutically acceptable salt thereof.

(28) Use of a compound having Rho kinase inhibitory activity for the production of an agent for improving a visual function disorder, which improves a visual function disorder caused by damage or degeneration of retinal nerve cell or optic nerve.

(29) Use of the above-mentioned (28), wherein the improvement of the visual function disorder is by way of promotion of extension of axon of a retinal ganglion cell.

(30) Use of the above-mentioned (28), wherein the improvement of the visual function disorder is by way of regeneration of an optic nerve cell.

(31) Use of a compound having Rho kinase inhibitory activity for the production of an agent for promoting extension of axon of a retinal ganglion cell.

(32) Use of a compound having Rho kinase inhibitory activity for the production of an agent for promoting the regeneration of an optic nerve cell.

(33) The use of any of the above-mentioned (28)–(32), wherein the compound having Rho kinase inhibitory activity is an amide compound represented by the above-mentioned formula (I), an isomer thereof and/or a pharmaceutically acceptable acid addition salt thereof, or a prodrug thereof.

(34) The use of any of the above-mentioned (28)–(32), wherein the compound having Rho kinase inhibitory activity is an amide compound represented by the above-mentioned formula (I'), an isomer thereof and/or a pharmaceutically acceptable acid addition salt thereof, or a prodrug thereof.

(35) The use of any of the above-mentioned (28)–(32), wherein the compound having Rho kinase inhibitory activity is (R)-(+)-N-(1H-pyrrolo[2,3-b]pyridin-4-yl)-4-(1-aminoethyl)benzamide or a pharmaceutically acceptable acid addition salt thereof, or a prodrug thereof, particularly (R)-(+)-N-(1H-pyrrolo[2,3-b]pyridin-4-yl)-4-(1-aminoethyl)benzamide monohydrochloride.

(36) The use of any of the above-mentioned (28)–(32), wherein the compound having Rho kinase inhibitory activity is a compound selected from thiochroman compounds, isoquinolinesulfonamide derivatives, vinylbenzene derivatives and ethacrynic acid or a pharmaceutically acceptable salt thereof.

In addition, with regard to the visual function impaired due to damage and/or degeneration of retinal nerve cell or optic nerve, the present invention provides a method for improving a visual function, use of a compound having Rho kinase inhibitory action for the production of a pharmaceutical agent to improve visual function, a composition for improving visual function and a commercial package containing a composition for improving visual function.

BRIEF DESCRIPTION OF THE DRAWINGS

In the Figures, compound 1 means (R)-(+)-N-(1H-pyrrolo[2,3-b]pyridin-4-yl)-4-(1-aminoethyl)benzamide dihydrochloride 3/2 hydrate, compound 2 means (R)-(+)-N-(1H-pyrrolo[2,3-b]pyridin-4-yl)-4-(1-aminoethyl)benzamide monohydrochloride, compound 3 means 4-[2-(2,3,4,5,6-pentafluorophenyl)acryloyl]cinnamic acid, compound 4 means ethacrynic acid, and compound 5 means fasudil hydrochloride.

DETAILED DESCRIPTION OF THE INVENTION

Figure 1:
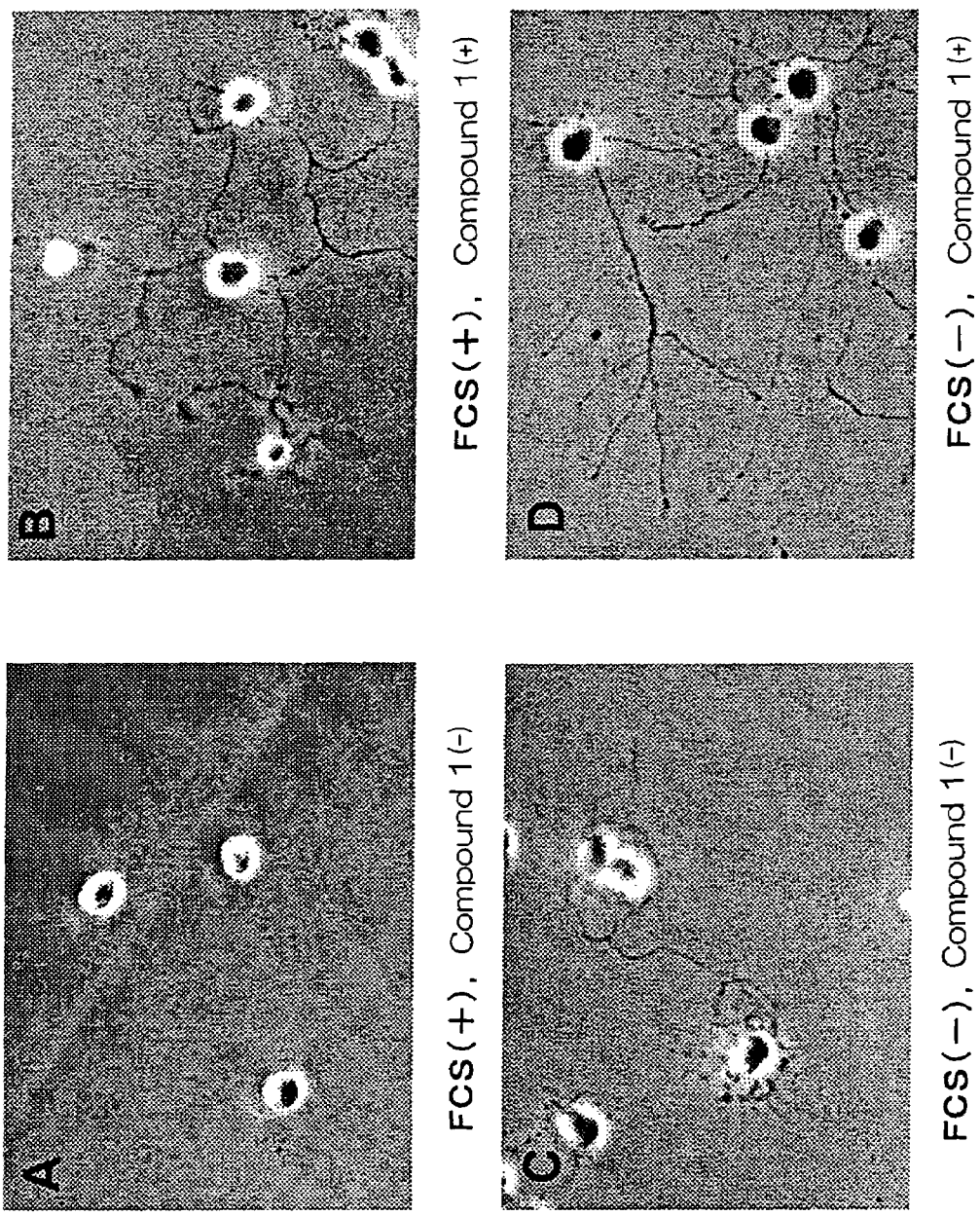
FIG. 1 shows a microscopic image indicating the level of extension of the nerve axon of retinal ganglion cell in the presence or absence of a Rho kinase inhibitor (compound 1), wherein A shows an image with the addition of fetal calf serum (FCS) and without addition of a Rho kinase inhibitor, B shows an image with the addition of FCS and a Rho kinase inhibitor, C shows an image without the addition of FCS and a Rho kinase inhibitor, and D shows an image without addition of FCS and with the addition of a Rho kinase inhibitor.

The visual function disorder in the present invention means a visual disorder or a disease with various symptoms of loss of vision, low vision, narrow vision, abnormal color sensation and misty vision, abnormal electroretinogram, and isually evoked potential and the like, which is caused by decreased retinal ganglion cells and optic nerve fibers due to damage, degeneration, and the like, of retinal nerve or optic nerve, optic atrophy, loss of nerve fibers axon, nerve fibers demyelination of optic nerve or defects of optic nerve, and which is specifically exemplified by a visual disorder accompanying damage due to retinal inflammation and the like (retinal neuropathy, retinal vascular occlusion, periphlebitis retinae, Eales' disease, ischemic ophthalmopathy, retinal arteriolar microaneurysm, retinopathy caused by hypertension, renal disease and blood disease, diabetic retinopathy, retinal dystrophy, macular dystrophy, chorioretinopathy, macular degeneration, macular edema, retinal pigment epithelium detachment, degenerative retinoschisis, retinoblastoma, retinal pigment epithelioma etc.) and the like; a visual disorder accompanying degeneration or damage of optic nerve (optic neuritis, capillary angioma of optic disc, ischemic optic neuropathy, defects of retinal nerve fibers layer, retinal optic atrophy, neurotmesis of optic nerve, traumatic optic neuropathy, choked disc, coloboma of optic disc, optic nerve hypoplasia, toxic optic atrophy etc.); visual disorder due to optic atrophy, degeneration and the like caused by elevated intraocular pressure (glaucoma etc.) and the like; and the like.

In the present invention, improvement of visual function disorder is intended to mean improving a visual disorder caused by damage, degeneration and the like of retinal nerve and optic nerve, by extension or promotion of extension of axon of a retinal ganglion cell, regeneration of optic nerve cell and the like. In addition, the present invention aims at providing a pharmaceutical agent having a promoting action on the extension of axon of a retinal ganglion cell and/or regenerative action of an optic nerve cell, and such pharmaceutical agent is also encompassed in the scope of the present invention.

Here, in the present invention, the "promotion of extension of axon" encompasses any state where the growth of axon is observed, such as neogenesis (regeneration), extension and the like of the axon in the earlier stages, not to mention the action of promotion of extension of axon of a retinal ganglion cell, namely, an action to elongate the axon and to form synapse. Therefore, even when simply referred with "an agent for promoting extension of axon" or "promotion of extension of axon" in the present specification, the agent means any agent that activates or induces neogenesis (regeneration), extension, promotion of extension and the like of the axon of retinal ganglion cell. Furthermore, by the neogenesis (regeneration) action of the optic nerve cell is meant an increase in the number of the optic nerve cells that have been retrogradely degenerated or decreased due to damage, degeneration and the like of the axon and by the "agent for promoting neogenesis of the optic nerve cell" is meant any agent that promotes an increase in the number of the regenerated optic nerve cells.

The compound having a Rho kinase inhibitory activity, which is used as an active ingredient in the present invention, may be any as long as it has a Rho kinase inhibitory activity. In the present invention, Rho kinase means serine/threonine kinase activated along with the activation of Rho. For example, ROKα (ROCKII: Leung, T. et al, J. Biol. Chem., 270, 29051–29054, 1995), p160 ROCK (ROKβ, ROCK-I: Ishizaki, T. et al, The EMBO J., 15(8), pp.1885–1893, 1996) and other proteins having a serine/threonine kinase activity are exemplified.

Examples of the compound having a Rho kinase inhibitory activity, which is used in the present invention, include the amide compound, isoquinolinesulfonamide derivative and isoquinoline derivative described in the above-mentioned WO98/06433, WO97/28130 and Naunyn-Schmiedeberg's Archives of Pharmacology 385(1), Suppl., R219 (1998), and vinyl benzene derivative and ethacrynic acid described in WO00/57914 and JP-A-2000-44513. In addition, the nitrogen-containing compound described in WO01/56988 can be also mentioned. Furthermore, the thiochroman compounds described in WO01/68607 can be mentioned.

As the aforementioned amide compound, for example, a compound of the above-mentioned formula (I), particularly a compound of the formula (I'), are used. As the aforementioned isoquinolinesulfonamide derivative, hexahydro-1-(5-isoquinolinesulfonyl)-1H-1,4-diazepine hydrochloride [fasudil hydrochloride] and the like are used. As the aforementioned isoquinoline derivative, hexahydro-1-[(4-methyl-5-isoquinolinyl)sulfonyl]-1H-1,4-diazepine dihydrochloride, (S)-(+)-hexahydro-2-methyl-1-[(4-methyl-5-isoquinolinyl)sulfonyl]-1H-1,4-diazepine hydrochloride, hexahydro-7-methyl-1-[(4-methyl-5-isoquinolinyl)sulfonyl]-1H-1,4-diazepine dihydrochloride, hexahydro-5-methyl-1-[(4-methyl-5-isoquinolinyl)sulfonyl]-1H-1,4-diazepine dihydrochloride, hexahydro-2-methyl-1-[(4-methyl-5-isoquinolinyl)sulfonyl]-1H-1,4-diazepine hydrochloride, (R)-(−)-hexahydro-2-methyl-1-[(4-methyl-5-isoquinolinyl)-sulfonyl]-1H-1,4-diazepine hydrochloride, (R)-(+)-hexahydro-5-methyl-1-[(4-methyl-5-isoquinolinyl)sulfonyl]-1H-1, 4-diazepine hydrochloride and the like are used.

As the aforementioned vinyl benzene derivative, 4-[2-(2, 3,4,5,6-pentafluorophenyl)acryloyl]cinnamic acid and the like are mentioned. As the aforementioned nitrogen-containing compound, N-[1-(3,5-dimethoxybenzyl)tetrahydro-1H-3-pyrrolyl]-N-(1H-5-indazolyl)amine and the like can be mentioned.

Preferred are the amide compound represented by the formula (I), isoquinolinesulfonamide derivative, vinylbenzene erivative and ethacrynic acid, and particularly preferred are the amide compound represented by the formula (I'), fasudil hydrochloride, ethacrynic acid and 4-[2-(2,3,4,5,6-pentafluorophenyl)acryloyl]cinnamic acid.

Further, as the aforementioned thiochroman compounds, the following compounds can be mentioned:
(S)-4-amino-N-(4-pyridyl)thiochroman-7-carboxamide,
(S)-4-amino-N-(4-pyridyl)thiochroman-7-carboxamide 1,1-dioxide,
(S)-4-amino-N-(1H-pyrazolo[3,4-b]pyridin-4-yl)thiochroman-7-carboxamide,
(S)-4-amino-N-(1H-pyrazolo[3,4-b]pyridin-4-yl)thiochroman-7-carboxamide 1,1-dioxide,
(S)-4-amino-N-(1H-pyrrolo[2,3-b]pyridin-4-yl)thiochroman-7-carboxamide,
(S)-4-amino-N-(1H-pyrrolo[2,3-b]pyridin-4-yl)thiochroman-7-carboxamide 1,1-dioxide,
(S)-4-amino-6-methyl-N-(4-pyridyl)thiochroman-7-carboxamide,
(S)-4-amino-6-methyl-N-(4-pyridyl)thiochroman-7-carboxamide 1,1-dioxide,
(S)-4-amino-6-chloro-N-(4-pyridyl)thiochroman-7-carboxamide,
(S)-4-amino-6-chloro-N-(4-pyridyl)thiochroman-7-carboxamide 1,1-dioxide,
(S)-4-amino-8-methyl-N-(4-pyridyl)thiochroman-7-carboxamide,
(S)-4-amino-8-methyl-N-(4-pyridyl)thiochroman-7-carboxamide 1,1-dioxide,
(S)-4-amino-6-methyl-N-(1H-pyrrolo[2,3-b]pyridin-4-yl) thiochroman-7-carboxamide 1,1-dioxide,
(S)-4-amino-6-chloro-N-(1H-pyrrolo[2,3-b]pyridin-4-yl) thiochroman-7-carboxamide 1,1-dioxide In the present invention, one kind of a compound having a Rho kinase inhibitory activity may be used alone, or, where necessary, several kinds may be concurrently used.

In the present invention, moreover, a compound having Rho kinase inhibitory activity, which is an effective component, and other visual function disorder improving agents can be used in combination.

In the present specification, each symbol of the formulas (I) and (I') is defined as follows.

Alkyl for R, R' and $R^1$ is linear or branched alkyl having 1 to 10 carbon atoms, which is exemplified by methyl, ethyl, propyl, isopropyl, butyl, isobutyl, sec-butyl, tert-butyl, pentyl, hexyl, heptyl, octyl, nonyl, decyl and the like, with preference given to alkyl having 1 to 4 carbon atoms.

Cycloalkyl for R, R' and $R^1$ has 3 to 7 carbon atoms and is exemplified by cyclopropyl, cyclobutyl, cyclopentyl, cyclohexyl, cycloheptyl and the like.

Cycloalkylalkyl for R, R' and $R^1$ is that wherein the cycloalkyl moiety is the above-mentioned cycloalkyl having 3 to 7 carbon atoms and the alkyl moiety is linear or branched alkyl having 1 to 6 carbon atoms (e.g., methyl, ethyl, propyl, isopropyl, butyl, pentyl, hexyl and the like), which is exemplified by cyclopropylmethyl, cyclobutylmethyl, cyclopentylmethyl, cyclohexylmethyl, cycloheptylmethyl, cyclopropylethyl, cyclobutylethyl, cyclopentylethyl, cyclohexylethyl, cycloheptylethyl, cyclopropylpropyl, cyclobutylpropyl, cyclopentylpropyl, cyclohexylpropyl, cycloheptylpropyl, cyclopropylbutyl, cyclobutylbutyl, cyclopentylbutyl, cyclohexylbutyl, cycloheptylbutyl, cyclopropylhexyl, cyclobutylhexyl, cyclopentylhexyl, cyclohexylhexyl, cycloheptylhexyl and the like.

Aralkyl for R, R' and $R^1$ is that wherein alkyl moiety is alkyl having 1 to 4 carbon atoms and is exemplified by phenylalkyl such as benzyl, 1-phenylethyl, 2-phenylethyl, 3-phenylpropyl, 4-phenylbutyl and the like.

The substituent of optionally substituted cycloalkyl, cycloalkylalkyl, phenyl and aralkyl on the ring for R, R' and $R^1$ is halogen (e.g., chlorine, bromine, fluorine and iodine), alkyl (same as alkyl for R, R' and $R^1$), alkoxy (linear or branched alkoxy having 1 to 6 carbon atoms, such as methoxy, ethoxy, propoxy, isopropoxy, butoxy, isobutoxy, sec-butoxy, tert-butoxy, pentyloxy, hexyloxy and the like), aralkyl (same as aralkyl for R, R' and R1) or haloalkyl (alkyl for R, R' and $R^1$ which is substituted by 1–5 halogen, and exemplified by fluoromethyl, difluoromethyl, trifluoromethyl, 2,2,2-trifluoroethyl, 2,2,3,3,3-pentafluoropropyl and the like), nitro, amino, cyano, azide and the like.

The group formed by R and $R^1$ or R' and $R^1$ in combination together with the adjacent nitrogen atom, which forms a heterocycle optionally further having, in the ring, oxygen atom, sulfur atom or optionally substituted nitrogen atom is preferably a 5 or 6-membered ring and condensed ring thereof. Examples thereof include 1-pyrrolidinyl, piperidino, 1-piperazinyl, morpholino, thiomorpholino, 1-imidazolyl, 2,3-dihydrothiazol-3-yl and the like. The substituent of the optionally substituted nitrogen atom is exemplified by alkyl, aralkyl, haloalkyl and the like. As used herein, alkyl, aralkyl and haloalkyl are as defined for R, R' and $R^1$.

Alkyl at $R^2$ is as defined for R, R' and $R^1$.

Halogen, alkyl, alkoxy and aralkyl at $R^3$ and $R^4$ are as defined for R, R' and $R^1$.

Acyl at $R^3$ and $R^4$ is alkanoyl having 2 to 6 carbon atoms (e.g., acetyl, propionyl, butyryl, valeryl, pivaloyl and the like), benzoyl or phenylalkanoyl wherein the alkanoyl moiety has 2 to 4 carbon atoms (e.g., phenylacetyl, phenylpropionyl, phenylbutyryl and the like).

Alkylamino at $R^3$ and $R^4$ is that wherein the alkyl moiety is linear or branched alkyl having 1 to 6 carbon atoms. Examples thereof include methylamino, ethylamino, propylamino, isopropylamino, butylamino, isobutylamino, sec-butylamino, tert-butylamino, pentylamino, hexylamino and the like.

Acylamino at $R^3$ and $R^4$ is that wherein acyl moiety is alkanoyl having 2 to 6 carbon atoms, benzoyl or the alkanoyl moiety is phenylalkanoyl having 2 to 4 carbon atoms and the like, which is exemplified by acetylamino, propionylamino, butyrylamino, valerylamino, pivaloylamino, benzoylamino, phenylacetylamino, phenylpropionylamino, phenylbutyrylamino and the like.

Alkylthio at $R^3$ and $R^4$ is that wherein the alkyl moiety is linear or branched alkyl having 1 to 6 carbon atoms, which is exemplified by methylthio, ethylthio, propylthio, isopropylthio, butylthio, isobutylthio, sec-butylthio, tert-butylthio, pentylthio, hexylthio and the like.

Aralkyloxy at $R^3$ and $R^4$ is that wherein the aralkyl moiety is aralkyl having $C_{1-4}$ alkyl, which is exemplified by benzyloxy, 1-phenylethyloxy, 2-phenylethyloxy, 3-phenylpropyloxy, 4-phenylbutyloxy and the like.

Aralkylthio at $R^3$ and $R^4$ is that wherein the aralkyl moiety is aralkyl having $C_{1-4}$ alkyl, which is exemplified by benzylthio, 1-phenylethylthio, 2-phenylethylthio, 3-phenylpropylthio, 4-phenylbutylthio and the like.

Alkoxycarbonyl at $R^3$ and $R^4$ isthat wherein the alkoxy moiety is linear or branched alkoxy having 1 to 6 carbon atoms, which is exemplified by methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, hexyloxycarbonyl and the like.

Mono- or di-alkylcarbamoyl at $R^3$ and $R^4$ is carbamoyl mono- or di-substituted by alkyl having 1 to 4 carbon atoms, which is exemplified by methylcarbamoyl, dimethylcarbamoyl, ethylcarbamoyl, diethylcarbamoyl, propylcarbamoyl, dipropylcarbamoyl, butylcarbamoyl, dibutylcarbamoyl and the like.

Alkoxy at $R^5$ is as defined for R, R' and $R^1$.

Alkoxycarbonyloxy at $R^5$ is that wherein the alkoxy moiety is linear or branched alkoxy having 1 to 6 carbon atoms, which is exemplified by methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, hexyloxycarbonyloxy and the like.

Alkanoyloxy at $R^5$ is that wherein the alkanoyl moiety is alkanoyl having 2 to 6 carbon atoms, which is exemplified by acetyloxy, propionyloxy, butyryloxy, valeryloxy, pivaloyloxy and the like.

Aralkyloxycarbonyloxy at $R^5$ is that wherein the aralkyl moiety is aralkyl having $C_1$–$C_4$ alkyl, which is exemplified by benzyloxycarbonyloxy, 1-phenylethyloxycarbonyloxy, 2-phenylethyloxycarbonyloxy, 3-phenylpropyloxycarbonyloxy, 4-phenylbutyloxycarbonyloxy and the like.

Alkyl for $R^6$ is as defined for R, R' and $R^1$; alkyl for $R^8$ and $R^9$ is as defined for R, R' and $R^1$; and aralkyl for $R^8$ and $R^9$ is as defined for R, R' and $R^1$.

Alkyl for $R^7$ is as defined for R, R' and $R^1$ and aralkyl for $R^7$ is as defined for R, R' and $R^1$.

The group formed by $R^6$ and $R^7$ in combination, which forms a heterocycle optionally further having, in the ring, oxygen atom, sulfur atom or optionally substituted nitrogen atom, is exemplified by imidazol-2-yl, thiazol-2-yl, oxazol-2-yl, imidazolin-2-yl, 3,4,5,6-tetrahydropyridin-2-yl, 3,4,5,6-tetrahydropyrimidin-2-yl, 1,3-oxazolin-2-yl, 1,3-thiazolin-2-yl or optionally substituted benzoimidazol-2-yl, benzothiazol-2-yl, benzoxazol-2-yl and the like having a substituent such as halogen, alkyl, alkoxy, haloalkyl, nitro, amino, phenyl, aralkyl and the like. As used herein, halogen, alkyl, alkoxy, haloalkyl and aralkyl are as defined for R, R' and $R^1$.

The substituent of the above-mentioned optionally substituted nitrogen atom is exemplified by alkyl, aralkyl, haloalkyl and the like. As used herein, alkyl, aralkyl and haloalkyl are as defined for R, R' and $R^1$.

Hydroxyalkyl for $R^{10}$ and $R^{11}$ is linear or branched alkyl having 1 to 6 carbon atoms which is substituted by 1 to 3 hydroxy, which is exemplified by hydroxymethyl, 2-hydroxyethyl, 1-hydroxyethyl, 3-hydroxypropyl, 4-hydroxybutyl and the like.

Alkyl for $R^{10}$ and $R^{11}$ is as defined for R, R' and $R^1$; haloalkyl and alkoxycarbonyl for $R^{10}$ and $R^{11}$ are as defined for R, R' and $R^1$; aralkyl for $R^{10}$ and $R^{11}$ is as defined for R, R' and $R^1$.

Cycloalkyl formed by $R^{10}$ and $R^{11}$ in combination is the same as cycloalkyl for R, R' and $R^1$.

Alkyl for L is as defined for R, R' and $R^1$.

Aminoalky for L is a linear or branched alkyl having 1 to 6 carbon atoms, which is substituted by amino, which is exemplified by aminomethyl, 2-aminoethyl, 1-aminoethyl, 3-aminopropyl, 4-aminobutyl, 5-aminopentyl, 6-aminohexyl and the like.

Mono- or dialkylaminoalkyl for L is mono- or di-substituted aminoalkyl with alkyl having 1 to 4 carbon atoms, which is exemplified by methylaminomethyl, dimethylaminomethyl, ethylaminomethyl, diethylaminomethyl, propylaminomethyl, dipropylaminomethyl, butylaminomethyl, dibutylaminomethyl, 2-dimethylaminoethyl, 2-diethylaminoethyl and the like.

Carbamoylalkyl for L is linear or branched alkyl having 1 to 6 carbon atoms substituted by carbamoyl, which is exemplified by carbamoylmethyl, 2-carbamoylethyl, 1-carbamoylethyl, 3-carbamoylpropyl, 4-carbamoylbutyl, 5-carbamoylpentyl, 6-carbamoylhexyl and the like.

Phthalimidoalkyl for L is linear or branched alkyl having 1 to 6 carbon atoms, which is substituted by phthalimide. Examples thereof include phthalimidomethyl, 2-phthalimidoethyl, 1-phthalimidoethyl, 3-phthalimidopropyl, 4-phthalimidobutyl, 5-phthalimidopentyl, 6-phthalimidohexyl and the like.

Alkyl for B is as defined for R, R' and $R^1$.
Alkoxy for B is as defined for R, R' and $R^1$.
Aralkyl for B is as defined for R, R' and $R^1$.
Aralkyloxy for B is as defined for $R^3$ and $R^4$.
Aminoalkyl for B is as defined for L.
Hydroxyalkyl for B is as defined for $R^{10}$ and $R^{11}$.

Alkanoyloxyalkyl for B is that wherein linear or branched alkyl having 1 to 6 carbon atoms is substituted by alkanoyloxy having alkanoyl moiety having 2 to 6 carbon atoms, which is exemplified by acetyloxymethyl, propionyloxymethyl, butyryloxymethyl, valeryloxymethyl, pivaloyloxymethyl, acetyloxyethyl, propionyloxyethyl, butyryloxyethyl, valeryloxyethyl, pivaloyloxyethyl and the like.

Alkoxycarbonylalkyl for B is that wherein linear or branched alkyl having 1 to 6 carbon atoms is substituted by alkoxycarbonyl having alkoxy moiety having 1 to 6 carbon atoms, which is exemplified by methoxycarbonylmethyl, ethoxycarbonylmethyl, propoxycarbonylmethyl, isopropoxycarbonylmethyl, butoxycarbonylmethyl, isobutoxycarbonylmethyl, sec-butoxycarbonylmethyl, tert-butoxycarbonylmethyl, pentyloxycarbonylmethyl, hexyloxycarbonylmethyl, methoxycarbonylethyl, ethoxycarbonylethyl, propoxycarbonylethyl, isopropoxycarbonylethyl, butoxycarbonylethyl, isobutoxycarbonylethyl, sec-butoxycarbonylethyl, tert-butoxycarbonylethyl, pentyloxycarbonylethyl, hexyloxycarbonylethyl and the like.

Halogen for $Q^1$, $Q^2$ and $Q^3$ is as defined for R, R' and $R^1$.
Aralkyloxy for $Q^1$ and $Q^2$ is as defined for $R^3$ and $R^4$.
Alkoxy for $Q^3$ is as defined for R, R' and $R^1$.

Alkylene for W, X and Y is linear or branched alkylene having 1 to 6 carbon atoms, which is exemplified by methylene, ethylene, trimethylene, propylene, tetramethylene, pentamethylene, hexamethylene and the like.

Alkenylene for Y is linear or branched alkenylene having 2 to 6 carbon atoms, which is exemplified by vinylene, propenylene, butenylene, pentenylene and the like.

Alkyl for Rb is as defined for R, R' and $R^1$.
Aralkyl for Rb is as defined for R, R' and $R^1$.
Aminoalkyl for Rb is as defined for L.
Mono- or dialkylaminoalkyl for Rb is as defined for L.

The nitrogen-containing heterocycle for Rc, when it is a monocyclic ring, is exemplified by pyridine, pyrimidine, pyridazine, triazine, pyrazole, triazole and the like, and when it is a condensed ring, it is exemplified by pyrrolopyridine (e.g., 1H-pyrrolo[2,3-b]pyridine, 1H-pyrrolo[3,2-b]pyridine, 1H-pyrrolo[3,4-b]pyridine and the like), pyrazolopyridine (e.g., 1H-pyrazolo[3,4-b]pyridine, 1H-pyrazolo[4,3-b]pyridine and the like), imidazopyridine (e.g., 1H-imidazo[4,5-b]pyridine and the like), pyrrolopyrimidine (e.g., 1H-pyrrolo[2,3-d]pyrimidine, 1H-pyrrolo[3,2-d]pyrimidine, 1H-pyrrolo[3,4-d]pyrimidine and the like), pyrazolopyrimidine (e.g., 1H-pyrazolo[3,4-d]pyrimidine, pyrazolo[1,5-a]pyrimidine, 1H-pyrazolo[4,3-d]pyrimidine and the like), imidazopyrimidine (e.g., imidazo[1,2-a]pyrimidine, 1H-imidazo[4,5-d]pyrimidine and the like), pyrrolotriazine (e.g., pyrrolo[1,2-a]-1,3,5-triazine, pyrrolo[2,1-f]-1,2,4-triazine), pyrazolotriazine (e.g., pyrazolo[1,5-a]-1,3,5-triazine and the like), triazolopyridine (e.g., 1H-1,2,3-triazolo[4,5-b]pyridine and the like), triazolopyrimidine (e.g., 1,2,4-triazolo[1,5-a]pyrimidine, 1,2,4-triazolo[4,3-a]pyrimidine, 1H-1,2,3-triazolo[4,5-d]pyrimidine and the like), cinnoline, quinazoline, quinoline, pyridopyridazine (e.g., pyrido[2,3-c]pyridazine and the like), pyridopyrazine (e.g., pyrido[2,3-b]pyrazine and the like), pyridopyrimidine (e.g., pyrido[2,3-d]pyrimidine, pyrido[3,2-d]pyrimidine and the like), pyrimidopyrimidine (e.g., pyrimido[4,5-d]pyrimidine, pyrimido[5,4-d]pyrimidine and the like), pyrazinopyrimidine (e.g., pyrazino[2,3-d]pyrimidine and the like), naphthyridine (e.g., 1,8-naphthyridine and the like), tetrazolopyrimidine (e.g., tetrazolo[1,5-a]pyrimidine and the like), thienopyridine (e.g., thieno[2,3-b]pyridine and the like), thienopyrimidine (e.g., thieno[2,3-d]pyrimidine and the like), thiazolopyridine (e.g., thiazolo[4,5-b]pyridine, thiazolo[5,4-b]pyridine and the like), thiazolopyrimidine (e.g., thiazolo[4,5-d]pyrimidine, thiazolo[5,4-d]pyrimidine and the like), oxazolopyridine (e.g., oxazolo[4,5-b]pyridine, oxazolo[5,4-b]pyridine and the like), oxazolopyrimidine (e.g., oxazolo[4,5-d]pyrimidine, oxazolo[5,4-d]pyrimidine and the like), furopyridine (e.g., furo[2,3-b]pyridine, furo[3,2-b]pyridine and the like), furopyrimidine (e.g., furo[2,3-d]pyrimidine, furo[3,2-d]pyrimidine and the like), 2,3-dihydropyrrolopyridine (e.g., 2,3-dihydro-1H-pyrrolo[2,3-b]pyridine, 2,3-dihydro-1H-pyrrolo[3,2-b]pyridine and the like), 2,3-dihydropyrrolopyrimidine (e.g., 2,3-dihydro-1H-pyrrolo[2,3-d]pyrimidine, 2,3-dihydro-1H-pyrrolo[3,2-d]pyrimidine and the like), 5,6,7,8-tetrahydropyrido[2,3-d]pyrimidine, 5,6,7,8-tetrahydro-1,8-naphthyridine, 5,6,7,8-tetrahydroquinoline and the like. When these rings form a hydrogenated aromatic ring, the carbon atom in the ring may be carbonyl and includes, for example, 2,3-dihydro-2-oxopyrrolopyridine, 2,3-dihydro-2,3-dioxopyrrolopyridine, 7,8-dihydro-7-oxo-1,8-naphthyridine, 5,6,7,8-tetrahydro-7-oxo-1,8-naphthyridine and the like.

These rings may be substituted by a substituent such as halogen, alkyl, alkoxy, aralkyl, haloalkyl, nitro, amino, alkylamino, cyano, formyl, acyl, aminoalkyl, mono- or dialkylaminoalkyl, azide, carboxy, alkoxycarbonyl, carbamoyl, mono- or di-alkylcarbamoyl, alkoxyalkyl (e.g., methoxymethyl, methoxyethyl, methoxypropyl, ethoxymethyl, ethoxyethyl, ethoxypropyl and the like), optionally substituted hydrazino and the like.

As used herein, the substituent of the optionally substituted hydrazino includes alkyl, aralkyl, nitro, cyano and the like, wherein alkyl and aralkyl are as defined for R, R' and $R^1$ and exemplified by methylhydrazino, ethylhydrazino, benzylhydrazino and the like.

The compound of the formula (I) is exemplified by the following compounds.
(1) 4-(2-pyridylcarbamoyl)piperidine
(2) 1-benzyloxycarbonyl-4-(4-pyridylcarbamoyl)piperidine
(3) 1-benzoyl-4-(4-pyridylcarbamoyl)piperidine
(4) 1-propyl-4-(4-pyridylcarbamoyl)piperidine
(5) 1-[3-(2-(2-thienylmethyl)phenoxy)-2-hydroxypropyl]-4-(4-pyridylcarbamoyl)piperidine
(6) 4-(4-pyridylcarbamoyl)piperidine
(7) 1-benzyl-4-(4-pyridylcarbamoyl)-1,2,5,6-tetrahydropyridine
(8) 3-(4-pyridylcarbamoyl)piperidine (9) 1-benzyl-3-(4-pyridylcarbamoyl)piperidine
(10) 1-(2-(4-benzyloxyphenoxy)ethyl)-4-(N-(2-pyridyl)-N-benzylcarbamoyl)piperidine
(11) 1-formyl-4-(4-pyridylcarbamoyl)piperidine
(12) 4-(3-pyridylcarbamoyl)piperidine
(13) 1-isopropyl-4-(4-pyridylcarbamoyl)piperidine
(14) 1-methyl-4-(4-pyridylcarbamoyl)piperidine
(15) 1-hexyl-4-(4-pyridylcarbamoyl)piperidine
(16) 1-benzyl-4-(4-pyridylcarbamoyl)piperidine
(17) 1-(2-phenylethyl)-4-(4-pyridylcarbamoyl)piperidine
(18) 1-(2-(4-methoxyphenyl)ethyl)-4-(4-pyridylcarbamoyl)-piperidine
(19) 1-(2-(4-methoxyphenyl)ethyl)-4-(2-pyridylcarbamoyl)-piperidine
(20) 1-(2-(4-chlorophenyl)ethyl)-4-(4-pyridylcarbamoyl)-piperidine
(21) 1-diphenylmethyl-4-(2-pyridylcarbamoyl)piperidine
(22) 1-[2-(4-(5-methyl-3-oxo-2,3,4,5-tetrahydropyridazin-6-yl)phenyl)ethyl]-4-(2-pyridylcarbamoyl)piperidine
(23) 1-(4-(4,5-dihydro-2-furyl)phenyl)-4-(4-pyridylcarbamoyl)piperidine
(24) 1-(2-nitrophenyl)-4-(4-pyridylcarbamoyl)piperidine
(25) 1-(2-aminophenyl)-4-(4-pyridylcarbamoyl)piperidine
(26) 1-nicotinoyl-4-(4-pyridylcarbamoyl)piperidine
(27) 1-isonicotinoyl-4-(4-pyridylcarbamoyl)piperidine
(28) 1-(3,4,5-trimethoxybenzoyl)-4-(4-pyridylcarbamoyl)-piperidine
(29) 1-acetyl-4-(4-pyridylcarbamoyl)piperidine
(30) 1-(3-(4-fluorobenzoyl)propyl)-4-(4-pyridylcarbamoyl)-piperidine
(31) 1-(3-(4-fluorobenzoyl)propyl)-4-(2-pyridylcarbamoyl)-piperidine
(32) 1-(1-(4-hydroxybenzoyl)ethyl)-4-(2-pyridylcarbamoyl)-piperidine
(33) 1-(1-(4-benzyloxybenzoyl)ethyl)-4-(2-pyridylcarbamoyl)-piperidine
(34) 1-(2-(4-hydroxyphenoxy)ethyl)-4-(2-pyridylcarbamoyl)-piperidine
(35) 1-(4-(4-fluorophenyl)-4-hydroxybutyl)-4-(4-pyridylcarbamoyl)piperidine
(36) 1-(1-methyl-2-(4-hydroxyphenyl)-2-hydroxyethyl)-4-(2-pyridylcarbamoyl)piperidine
(37) 1-cinnamyl-4-(2-pyridylcarbamoyl)piperidine
(38) 1-(2-hydroxy-3-phenoxypropyl)-4-(4-pyridylcarbamoyl)-piperidine
(39) 1-(2-hydroxy-3-phenoxypropyl)-4-(3-pyridylcarbamoyl)-piperidine
(40) 1-(2?-hydroxy-3-phenoxypropyl)-4-(2-pyridylcarbamoyl)-piperidine
(41) 1-(2-phenylethyl)-4-[N-(2-pyridyl)-N-(2-(N,N-dimethylamino)ethyl)carbamoyl]piperidine
(42) 1-benzyloxycarbonyl-4-(2-pyridylcarbamoyl)piperidine
(43) 1-(3-chlorophenyl)carbamoyl-4-(4-pyridylcarbamoyl)-piperidine
(44) 4-[N-(2-pyridyl)-N-(2-(N,N-dimethylamino)ethyl)-carbamoyl]piperidine
(45) 1-methyl-4-(4-pyridylcarbamoyl)-1,2,5,6-tetrahydropyridine
(46) 1-nicotinoyl-3-(4-pyridylcarbamoyl)piperidine
(47) 1-[2-(4-fluorobenzoyl)ethyl]-4-(4-pyridylcarbamoyl)-piperidine
(48) 1-(6-chloro-2-methylimidazo[1,2-a]pyridine-3-carbonyl)-4-(4-pyridylcarbamoyl)piperidine
(49) 1-(4-nitrobenzyl)-4-(4-pyridylcarbamoyl)piperidine
(50) 1-hexyl-4-(4-pyridylcarbamoyl)piperidine
(51) 1-benzyloxycarbonyl-4-(2-chloro-4-pyridylcarbamoyl)-piperidine
(52) 4-(2-chloro-4-pyridylcarbamoyl)piperidine
(53) 1-(2-chloronicotinoyl)-4-(4-pyridylcarbamoyl)piperidine
(54) 3-(2-chloro-4-pyridylcarbamoyl)piperidine
(55) 1-(4-phthalimidobutyl)-4-(4-pyridylcarbamoyl)piperidine
(56) 1-(3,5-di-tert-butyl-4-hydroxycinnamoyl)-4-(4-pyridylcarbamoyl)piperidine
(57) 1-carbamoylmethyl-4-(4-pyridylcarbamoyl)piperidine
(58) 1-benzyloxycarbonyl-4-(5-nitro-2-pyridylcarbamoyl)-piperidine
(59) 4-(5-nitro-2-pyridylcarbamoyl)piperidine
(60) trans-4-benzyloxycarboxamidomethyl-1-(4-pyridylcarbamoyl)cyclohexane
(61) trans-4-aminomethyl-1-(4-pyridylcarbamoyl)cyclohexane
(62) trans-4-formamidomethyl-1-(4-pyridylcarbamoyl)-cyclohexane
(63) trans-4-dimethylaminomethyl-1-(4-pyridylcarbamoyl)-cyclohexane
(64) N-benzylidene-trans-(4-pyridylcarbamoyl)-cyclohexylmethylamine
(65) trans-4-benzylaminomethyl-1-(4-pyridylcarbamoyl)-cyclohexane
(66) trans-4-isopropylaminomethyl-1-(4-pyridylcarbamoyl)-cyclohexane
(67) trans-4-nicotinoylaminomethyl-1-(4-pyridylcarbamoyl)-cyclohexane
(68) trans-4-cyclohexylaminomethyl-1-(4-pyridylcarbamoyl)-cyclohexane
(69) trans-4-benzyloxycarboxamide-1-(4-pyridylcarbamoyl)-cyclohexane
(70) trans-4-amino-1-(4-pyridylcarbamoyl)cyclohexane
(71) trans-4-(1-aminoethyl)-1-(4-pyridylcarbamoyl)cyclohexane
(72) trans-4-aminomethyl-cis-2-methyl-1-(4-pyridylcarbamoyl)-cyclohexane
(73) (+)-trans-4-(1-benzyloxycarboxamidopropyl)-1-cyclohexanecarboxylic acid
(74) (+)-trans-4-(1-benzyloxycarboxamidopropyl)-1-(4-pyridylcarbamoyl)cyclohexane
(75) (−)-trans-4-(1-benzyloxycarboxamidopropyl)-1-(4-pyridylcarbamoyl)cyclohexane
(76) (+)-trans-4-(1-aminopropyl)-1-(4-pyridylcarbamoyl)-cyclohexane
(77) (−)-trans-4-(1-aminopropyl)-1-(4-pyridylcarbamoyl)-cyclohexane
(78) (−)-trans-4-(1-benzyloxycarboxamidoethyl)-1-(4-pyridylcarbamoyl)cyclohexane
(79) (+)-trans-4-(1-benzyloxycarboxamidoethyl)-1-(4-pyridylcarbamoyl)cyclohexane
(80) (+)-trans-4-(1-aminoethyl)-1-(4-pyridylcarbamoyl)-cyclohexane
(81) (−)-trans-4-(1-aminoethyl)-1-(4-pyridylcarbamoyl)-cyclohexane
(82) trans-4-(4-chlorobenzoyl)aminomethyl-1-(4-pyridylcarbamoyl)cyclohexane
(83) trans-4-aminomethyl-1-(2-pyridylcarbamoyl)cyclohexane
(84) trans-4-benzyloxycarboxamidomethyl-1-(2-pyridylcarbamoyl)cyclohexane
(85) trans-4-methylaminomethyl-1-(4-pyridylcarbamoyl)-cyclohexane
(86) trans-4-(N-benzyl-N-methylamino)methyl-1-(4-pyridylcarbamoyl)cyclohexane

(87) trans-4-aminomethyl-1-(3-pyridylcarbamoyl)cyclohexane
(88) trans-4-aminomethyl-1-[(3-hydroxy-2-pyridyl)carbamoyl]-cyclohexane
(89) trans-4-benzyloxycarboxamidomethyl-1-(3-pyridylcarbamoyl)cyclohexane
(90) trans-4-benzyloxycarboxamidomethyl-1-[(3-benzyloxy-2-pyridyl)carbamoyl]cyclohexane
(91) trans-4-phthalimidomethyl-1-(4-pyridylcarbamoyl)-cyclohexane
(92) trans-4-benzyloxycarboxamidomethyl-1-(3-methyl-4-pyridylcarbamoyl)cyclohexane
(93) trans-4-aminomethyl-1-(3-methyl-4-pyridylcarbamoyl)-cyclohexane
(94) 4-(trans-4-benzyloxycarboxamidomethylcyclohexylcarbonyl)amino-2,6-dimethylpyridine-N-oxide
(95) 4-(trans-4-aminomethylcyclohexylcarbonyl)amino-2,6-dimethylpyridine-N-oxide
(96) trans-4-aminomethyl-1-(2-methyl-4-pyridylcarbamoyl)-cyclohexane
(97) trans-4-(1-benzyloxycarboxamidoethyl)-1-(4-pyridylcarbamoyl)cyclohexane
(98) trans-4-(1-amino-1-methylethyl)-1-(4-pyridylcarbamoyl)-cyclohexane
(99) trans-4-(2-aminoethyl)-1-(4-pyridylcarbamoyl)cyclohexane
(100) trans-4-(2-amino-1-methylethyl)-1-(4-pyridylcarbamoyl)-cyclohexane
(101) trans-4-(1-aminopropyl)-1-(4-pyridylcarbamoyl)-cyclohexane
(102) trans-4-aminomethyl-trans-1-methyl-1-(4-pyridylcarbamoyl)cyclohexane
(103) trans-4-benzylaminomethyl-cis-2-methyl-1-(4-pyridylcarbamoyl)cyclohexane
(104) trans-4-(1-benzyloxycarboxamide-1-methylethyl)-1-(4-pyridylcarbamoyl)cyclohexane
(105) trans-4-benzyloxycarboxamidomethyl-1-(N-methyl-4-pyridylcarbamoyl)cyclohexane
(106) trans-4-(1-acetamide-1-methylethyl)-1-(4-pyridylcarbamoyl)cyclohexane
(107) trans-N-(6-amino-4-pyrimidyl)-4-aminomethylcyclohexanecarboxamide
(108) trans-N-(1H-pyrrolo[2,3-b]pyridin-4-yl)-4-aminomethyl-cyclohexanecarboxamide
(109) (+)-trans-N-(1H-pyrrolo[2,3-b]pyridin-4-yl)-4-(1-aminoethyl)cyclohexanecarboxamide
(110) trans-N-(1H-pyrrolo[2,3-b]pyridin-4-yl)-4-(1-amino-1-methylethyl)cyclohexanecarboxamide
(111) trans-N-(1H-pyrazolo[3,4-b]pyridin-4-yl)-4-aminomethyl-cyclohexanecarboxamide
(112) (+)-trans-N-(1H-pyrazolo[3,4-b]pyridin-4-yl)-4-(1-aminoethyl)cyclohexanecarboxamide
(113) trans-N-(1H-pyrazolo[3,4-b]pyridin-4-yl)-4-(1-amino-1-methylethyl)cyclohexanecarboxamide
(114) (+)-trans-N-(2-amino-4-pyridyl)-4-(1-aminoethyl)-cyclohexanecarboxamide
(115) trans-N-(1H-pyrazolo[3,4-d]pyrimidin-4-yl)-4-aminomethylcyclohexanecarboxamide
(116) (+)-trans-N-(1H-pyrazolo[3,4-d]pyrimidin-4-yl)-4-(1-aminoethyl)cyclohexanecarboxamide
(117) trans-N-(1H-pyrazolo[3,4-d]pyrimidin-4-yl)-4-(1-amino-1-methylethyl)cyclohexanecarboxamide
(118) trans-N-(4-pyrimidinyl)-4-aminomethylcyclohexanecarboxamide
(119) trans-N-(3-amino-4-pyridyl)-4-aminomethylcyclohexane-carboxamide
(120) trans-N-(7H-imidazo[4,5-d]pyrimidin-6-yl)-4-aminomethylcyclohexanecarboxamide
(121) trans-N-(3H-1,2,3-triazolo[4,5-d]pyrimidin-7-yl)-4-aminomethylcyclohexanecarboxamide
(122) trans-N-(1-benzyl-1H-pyrazolo[3,4-b]pyridin-4-yl)-4-aminomethylcyclohexanecarboxamide
(123) trans-N-(1H-5-pyrazolyl)-4-aminomethylcyclohexane-carboxamide
(124) trans-N-(1H-pyrazolo[3,4-b]pyridin-4-yl)-4-aminomethyl-cyclohexanecarboxamide
(125) trans-N-(4-pyridazinyl)-4-aminomethylcyclohexanecarboxamide
(126) trans-N-(7H-pyrrolo[2,3-d]pyrimidin-4-yl)-4-aminomethylcyclohexanecarboxamide
(127) trans-N-(2-amino-4-pyridyl)-4-aminomethylcyclohexane-carboxamide
(128) trans-N-(thieno[2,3-d]pyrimidin-4-yl)-4-aminomethyl-cyclohexanecarboxamide
(129) trans-N-(5-methyl-1,2,4-triazolo[1,5-a]pyrimidin-7-yl)-4-aminomethylcyclohexanecarboxamide
(130) trans-N-(3-cyano-5-methylpyrazolo[1,5-a]pyrimidin-7-yl)-4-aminomethylcyclohexanecarboxamide
(131) trans-N-(1H-pyrazolo[3,4-b]pyridin-4-yl)-4-(1-amino-1-methylethyl)cyclohexanecarboxamide
(132) trans-N-(2-(1-pyrrolidinyl)-4-pyridyl)-4-aminomethyl-cyclohexanecarboxamide
(133) trans-N-(2,6-diamino-4-pyrimidyl)-4-aminomethylcyclohexanecarboxamide
(134) (+)-trans-N-(7-methyl-1,8-naphthyridin-4-yl)-4-(1-aminoethyl)cyclohexanecarboxamide
(135) trans-N-(1-benzyloxymethylpyrrolo[2,3-b]pyridin-4-yl)-4-aminomethylcyclohexanecarboxamide
(136) (+)-trans-N-(1-methylpyrrolo[2,3-b]pyridin-4-yl)-4-(1-aminoethyl)cyclohexanecarboxamide
(137) trans-N-benzyl-N-(2-benzylamino-4-pyridyl)-4-(1-amino-1-methylethyl)cyclohexanecarboxamide
(138) trans-N-(2-azide-4-pyridyl)-4-aminomethylcyclohexane-carboxamide
(139) trans-N-(2,3-dihydro-1H-pyrrolo[2,3-b]pyridin-4-yl)-4-aminomethylcyclohexanecarboxamide
(140) trans-N-(2,3-dihydro-1H-pyrrolo[2,3-b]pyridin-4-yl)-4-(1-amino-1-methylethyl)cyclohexanecarboxamide
(141-1) trans-N-(2-carboxy-4-pyridyl)-4-aminomethylcyclohexanecarboxamide
(141-2) (R)-(+)-trans-N-(3-bromo-1H-pyrrolo[2,3-b]pyridin-4-yl)-4-(1-aminoethyl)cyclohexanecarboxamide
(142) trans-N-(1H-pyrrolo[2,3-b]pyridin-4-yl)-4-guanidinomethylcyclohexanecarboxamide
(143) trans-N-(1H-pyrazolo[3,4-b]pyridin-4-yl)-4-guanidinomethylcyclohexanecarboxamide
(144) trans-N-(4-pyridyl)-4-guanidinomethylcyclohexane-carboxamide
(145) trans-N-(1-methylpyrrolo[2,3-b]pyridin-4-yl)-4-(guanidinomethyl)cyclohexanecarboxamide
(146) trans-N-(1H-pyrrolo[2,3-b]pyridin-4-yl)-4-(2-imidazolin-2-yl)aminomethylcyclohexanecarboxamide
(147) trans-N-(1-benzyloxymethylpyrrolo[2,3-b]pyridin-4-yl)-4-guanidinomethylcyclohexanecarboxamide
(148) trans-N-(2-amino-4-pyridyl)-4-guanidinomethylcyclohexanecarboxamide
(149) trans-N-(1-benzyloxymethyl-1H-pyrrolo[2,3-b]pyridin-4-yl)-4-(2-imidazolin-2-yl)aminomethylcyclohexanecarboxamide
(150) trans-N-(1H-pyrrolo[2,3-b]pyridin-4-yl)-4-(3-benzylguanidinomethyl)cyclohexanecarboxamide
(151) trans-N-(1H-pyrrolo[2,3-b]pyridin-4-yl)-4-(3-phenylguanidinomethyl)cyclohexanecarboxamide (152) trans-N-(1H-pyrrolo[2,3-b]pyridin-4-yl)-4-(3-propylguanidinomethyl)cyclohexanecarboxamide
(153) trans-N-(1H-pyrrolo[2,3-b]pyridin-4-yl)-4-(3-octylguanidinomethyl)cyclohexanecarboxamide
(154) trans-N-(1-benzyloxymethylpyrrolo[2,3-b]pyridin-4-yl)-4-(2-benzyl-3-ethylguanidinomethyl)cyclohexanecarboxamide
(155) trans-N-(1H-pyrrolo[2,3-b]pyridin-4-yl)-4-(imidazol-2-yl)aminomethylcyclohexanecarboxamide
(156) trans-N-(1H-pyrrolo[2,3-b]pyridin-4-yl)-4-(thiazol-2-yl)aminomethylcyclohexanecarboxamide
(157) (R)-(+)-N-(4-pyridyl)-4-(1-aminoethyl)benzamide
(158) N-(4-pyridyl)-4-(1-amino-1-methylethyl)benzamide
(159) N-(4-pyridyl)-4-aminomethyl-2-benzyloxybenzamide
(160) N-(4-pyridyl)-4-aminomethyl-2-ethoxybenzamide
(161) (R)-(−)-N-(4-pyridyl)-4-(1-aminoethyl)-3-nitrobenzamide
(162) (R)-(−)-N-(4-pyridyl)-3-amino-4-(1-aminoethyl)benzamide
(163) (R)-(+)-N-(4-pyridyl)-4-(1-aminoethyl)-3-chlorobenzamide
(164) N-(4-pyridyl)-3-aminomethylbenzamide
(165) (R)-(+)-N-(1H-pyrrolo[2,3-b]pyridin-4-yl)-4-(1-aminoethyl)benzamide
(166) (R)-(+)-N-(1H-pyrazolo[3,4-b]pyridin-4-yl)-4-(1-aminoethyl)benzamide
(167) N-(1H-pyrazolo[3,4-b]pyridin-4-yl)-4-guanidinomethylbenzamide
(168) N-(4-pyridyl)-4-guanidinomethylbenzamide
(169) (R)-(+)-N-(4-pyridyl)-4-(1-aminoethyl)-3-fluorobenzamide
(170) N-(4-pyridyl)-4-aminomethylbenzamide
(171) N-(4-pyridyl)-4-aminomethyl-2-hydroxybenzamide
(172) N-(4-pyridyl)-4-(2-aminoethyl)benzamide
(173) N-(4-pyridyl)-4-aminomethyl-3-nitrobenzamide
(174) N-(4-pyridyl)-3-amino-4-aminomethylbenzamide
(175) (S)-(−)-N-(4-pyridyl)-4-(1-aminoethyl)benzamide
(176) (S)-(−)-N-(4-pyridyl)-2-(1-aminoethyl)benzamide
(177) (R)-(+)-N-(4-pyridyl)-4-(1-aminoethyl)-2-chlorobenzamide
(178) (R)-(+)-N-(1H-pyrrolo[2,3-b]pyridin-4-yl)-4-(1-(3-propylguanidino)ethyl)benzamide
(179) (R)-(−)-N-(1H-pyrrolo[2,3-b]pyridin-4-yl)-4-(1-aminoethyl)-3-azidebenzamide
(180) (R)-(+)-N-(4-pyridyl)-4-(1-aminoethyl)-2-nitrobenzamide
(181) (R)-(−)-N-(4-pyridyl)-4-(1-aminoethyl)-3-ethoxybenzamide
(182) (R)-(+)-N-(3-iodo-1H-pyrrolo[2,3-b]pyridin-4-yl)-4-(1-aminoethyl)benzamide
(183) (R)-(+)-N-(3-iodo-1H-pyrrolo[2,3-b]pyridin-4-yl)-4-(1-aminoethyl)-3-azidebenzamide
(184) (R)-(−)-N-(4-pyridyl)-4-(1-aminoethyl)-3-hydroxybenzamide
(185) N-(1H-pyrazolo[3,4-b]pyridin-4-yl)-4-guanidinomethyl-3-nitrobenzamide
(186) (R)-N-(1H-pyrazolo[3,4-b]pyridin-4-yl)-4-(1-guanidinoethyl)-3-nitrobenzamide
(187) (R)-N-(1H-pyrazolo[3,4-b]pyridin-4-yl)-4-(1-aminoethyl)-2-nitrobenzamide
(188) N-(1H-pyrazolo[3,4-b]pyridin-4-yl)-4-guanidinobenzamide
(189) (R)-N-(1H-pyrazolo[3,4-b]pyridin-4-yl)-4-(1-aminoethyl)-3-nitrobenzamide
(190) (R)-N-(1H-pyrazolo[3,4-b]pyridin-4-yl)-4-(1-guanidinoethyl)benzamide
(191) N-(1H-pyrazolo[3,4-b]pyridin-4-yl)-4-(1-amino-2-hydroxyethyl)benzamide
(192) N-(1H-pyrazolo[3,4-b]pyridin-4-yl)-4-aminomethyl-3-nitrobenzamide
(193) N-(1H-pyrrolo[2,3-b]pyridin-4-yl)-4-piperidinecarboxamide
(194) N-(1H-pyrazolo[3,4-b]pyridin-4-yl)-4-piperidinecarboxamide
(195) N-(1H-pyrazolo[3,4-b]pyridin-4-yl)-1-aminoacetyl-4-iperidinecarboxamide
(196) N-(1-methoxymethyl-1H-pyrazolo[3,4-b]pyridin-4-yl)-4-piperidinecarboxamide
(197) N-(2,3-dihydro-1H-pyrrolo[2,3-b]pyridin-4-yl)-4-piperidinecarboxamide
(198) N-(1H-pyrrolo[2,3-b]pyridin-4-yl)-1-(2-phenylethyl)-4-piperidinecarboxamide
(199) N-(1H-pyrrolo[2,3-b]pyridin-4-yl)-1-amidino-4-piperidinecarboxamide
(200) N-(1H-pyrrolo[2,3-b]pyridin-4-yl)-1-(3-phenylpropyl)-4-piperidinecarboxamide
(201) N-(1H-pyrrolo[2,3-b]pyridin-4-yl)-1-benzyl-4-piperidinecarboxamide
(202) N-(1H-pyrazolo[3,4-b]pyridin-4-yl)-1-(2-phenylethyl)-4-piperidinecarboxamide
(203) N-(1H-pyrazolo[3,4-b]pyridin-4-yl)-1-(3-phenylpropyl)-4-piperidinecarboxamide
(204) N-(1H-pyrrolo[2,3-b]pyridin-4-yl)-4-(1-amino-1-methylethyl)benzamide Preferred are compounds (80), (109), (110), (112), (115), (142), (143), (144), (145), (153), (157), (163), (165), (166) and (179). More preferred are compound (165) and hydrochloride thereof, and particularly preferred is monohydrochloride of compound (165).

The compound having a Rho kinase inhibitory activity may be a pharmaceutically acceptable acid addition salt, wherein the acid is exemplified by inorganic acid such as hydrochloric acid, hydrobromic acid, sulfuric acid and the like, and organic acid such as methanesulfonic acid, fumaric acid, maleic acid, mandelic acid, citric acid, tartaric acid, salicylic acid and the like. A compound having a carboxyl group can be converted to a salt with a metal such as sodium, potassium, calcium, magnesium, aluminum and the like, a salt with an amino acid such as lysine and the like. Further, monohydrate, dihydrate, 1/2 hydrate, 1/3 hydrate, 1/4 hydrate, 2/3 hydrate, 3/2 hydrate, 6/5 hydrate and the like are encompassed in the present invention.

The compound to be used as a compound having Rho kinase inhibitory activity of the present invention may be provided as a prodrug. As used herein, the prodrug is a compound that can be converted to the aforementioned compound having Rho kinase inhibitory activity in living organisms, and, for example, a compound wherein a moiety in the molecule of the compound of the formula (I), such as carboxyl group (COOH), hydroxyl group (OH), amino group ($NH_2$, including amide), mercapto group (SH) and the like, is modified (Development of Pharmaceutical Product, vol. 7 (molecule design) Hirokawa Shoten).

The compound of the formula (I) can be synthesized by a method described in, for example, JP-A-62-89679, JP-A-3-218356, JP-A-5-194401, JP-A-6-41080, WO95/28387, WO98/06433 and the like. The thiochroman compounds can be synthesized by a method described in WO01/68607 and the like, the isoquinolinesulfonamide derivative can be synthesized by a method described in U.S. Pat. No. 4,678,783 and the like, and vinylbenzene derivative can be synthesized by a method described in JP-A-2000-44513 and the like.

When the above-mentioned compound having a Rho kinase inhibitory activity has an optical isomer, its racemate or cis-trans isomers, all of them can be used in the present invention. These isomers can be isolated by a conventional method or can be produced using starting materials of the isomers.

The acid addition salt, hydrate and prodrug can be produced by a conventional method.

When a compound having Rho kinase inhibitory activity is used as a pharmaceutical agent, particularly, as a visual function disorder improving agent or an agent for promoting extension of axon of a retinal ganglion cell or an agent for promoting regeneration of an optic nerve cell of the present invention, it is prepared as a general pharmaceutical preparation.

For example, the compound having a Rho kinase inhibitory activity is mixed with a carrier acceptable for formulation of a preparation (e.g., excipient, binder, disintegrator, corrective, corrigent, emulsifier, diluent, solubilizer and the like) to give a pharmaceutical composition, which is formulated into a preparation in the form suitable for oral or parenteral preparation, such as tablet, pill, powder, granule, capsule, troche, syrup, liquid, emulsion, suspension, injection (e.g., liquid, suspension and the like), suppository, inhalant, percutaneous absorber, eye drop, eye ointment, preparation to be embedded in the eye and the like.

When preparing a solid preparation, additives such as sucrose, lactose, cellulose sugar, D-mannitol, maltitol, dextran, starches, agar, arginates, chitins, chitosans, pectines, tragacanth gum, gum arabic, gelatins, collagens, casein, albumin, calcium phosphate, sorbitol, glycine, carboxymethylcellulose, polyvinylpyrrolidone, hydroxypropylcellulose, hydroxypropylmethylcellulose, glycerol, polyethylene glycol, sodium hydrogencarbonate, magnesium stearate, talc and the like are used. Tablets can be applied with a typical coating, where necessary, to give sugar coated tablets, enteric tablets, film-coated tablets, two-layer tablets and multi-layer tablets.

When preparing a semi-solid preparation, animal and plant fats and oils (e.g., olive oil, corn oil, castor oil and the like), mineral fats and oils (e.g., petrolatum, white petrolatum, solid paraffin and the like), wax (e.g., jojoba oil, carnauba wax, bee wax and the like), partly or entirely synthesized glycerol fatty acid esters (e.g., lauric acid, myristic acid, palmitic-acid and the like), and the like are used. Examples of commercially available products of these include Witepsol (manufactured by Dynamitnovel Ltd.), Farmazol (manufactured by NOF Corporation) and the like.

When preparing a liquid preparation, an additive, such as sodium chloride, glucose, sorbitol, glycerol, olive oil, propylene glycol, ethyl alcohol and the like, is used. When preparing an injection, a sterile aqueous solution such as physiological saline, isotonic solution, oily solution (e.g., sesame oil and soybean oil) and the like are used. Where necessary, a suitable suspending agent such as sodium carboxymethylcellulose, nonionic surfactant, solubilizer (e.g., benzyl benzoate and benzyl alcohol), and the like can be concurrently used. Moreover, when an eye drop is prepared, an aqueous liquid or solution is used, which is particularly a sterile injectable aqueous solution. The eye drop can appropriately contain various additives such as buffer (borate buffer, acetate buffer, carbonate buffer, sodium dihydrogen phosphate, disodium hydrogen phosphate and the like are preferable for reducing irritation), isotonicity agent (sodium chloride, conc. grycerol, mannitol, glucose and the like), solubilizer, preservative (chlorobutanol, benzyl alcohol, sodium dehydroacetate, benzalkonium chloride, boric acid and the like), thickener (hydroxyethylcellulose, hydroxypropylcellulose, hydroxypropylmethyl cellulose, polyvinyl alcohol, polyethylene glycol) and the like, chelating agent (sodium edetate, sodium citrate and the like), pH adjusting agent (generally, pH is preferably adjusted to about 6–8 by hydrochloric acid, sodium hydroxide, phosphoric acid or acetic acid) and aromatic.

When a preparation to be embedded in the eye is to be produced, a biodegradable polymer, such as polylactic acid, polyglycolic acid, lactic acid-glycolic acid copolymer, hydroxypropyl cellulose and the like, can be used.

The dose of the active ingredient of these preparations, is 0.1–100 wt %, suitably 1–50 wt %, of the preparation. While the dose varies depending on the symptom, body weight, age and the like of patients, it is generally about 1–500 mg a day for an adult, which is administered once to several times a day.

For topical administration into the eye drop, an eye drop containing a compound having Rho kinase inhibitory activity in a proportion of about 0.0001-about 10 w/v %, preferably about 0.001-about 1 w/v %, is preferably administered by several drops, preferably 1–3 drops, per administration several times, preferably 1–6 times, per one day. For administration as a preparation to be embedded in the eye, a preparation to be embedded in the eye, which contains a compound having Rho kinase inhibitory activity in a proportion of about 0.0001-about 1 mg, preferably about 0.001-about 0.5 mg, is prepared into a short rod, a needle, a film, a tablet, a microcapsule or fine sphere and the like according to the method described in, for example, JP-A-1-216917, JP-A-3-170418 (corresponding to EP430539 and U.S. Pat. No. 5,164,188) and JP-A-5-17370 (corresponding to EP488401 and U.S. Pat. No. 5,501,856) and the like and, for example, preferably buried in the vitreous body.

EXAMPLES

The present invention is explained in detail by referring to formulation examples and pharmacological action. The present invention is not limited in any way by the examples.

In the following Preparative Formulation Examples and Experimental Examples, a compound having Rho kinase inhibitory activity, such as (R)-(+)-N-(1H-pyrrolo[2,3-b]pyridin-4-yl)-4-(1-aminoethyl)benzamide dihydrochloride 3/2 hydrate (hereinafter to be also referred to as compound 1), (R)-(+)-N-(1H-pyrrolo[2,3-b]pyridin-4-yl)-4-(1-aminoethyl)benzamide monohydrochloride (hereinafter to be also referred to as compound 2), 4-[2-(2,3,4,5,6-pentafluorophenyl)acryloyl]cinnamic acid (hereinafter to be also referred to as compound 3), ethacrynic acid (hereinafter to be also referred to as compound 4) or fasudil hydrochloride (hereinafter to be also referred to as compound 5), was used.

Formulation Example 1

Tablet

| | |
|---|---|
| Compound of the present invention (compound 1) | 10.0 mg |
| Lactose | 50.0 mg |
| Cornstarch | 20.0 mg |
| Crystalline cellulose | 29.7 mg |
| Polyvinylpyrrolidone K30 | 5.0 mg |
| Talc | 5.0 mg |
| Magnesium stearate | 0.3 mg |
| | 120.0 mg |

The compound of the present invention (compound 1), lactose, cornstarch and crystalline cellulose were mixed, kneaded with polyvinylpyrrolidone K30 paste solution and passed through a 20-mesh sieve for granulation. After drying at 50° C. for 2 hours, the granules were passed through a 24-mesh sieve, and talc and magnesium stearate were added. Using a ϕ7 mm punch, tablets weighing 120 mg per tablet were prepared.

Formulation Example 2

Capsules

| Compound of the present invention (compound 1) | 10.0 mg |
| --- | --- |
| Lactose | 70.0 mg |
| Cornstarch | 35.0 mg |
| Polyvinylpyrrolidone K30 | 2.0 mg |
| Talc | 2.7 mg |
| Magnesium stearate | 0.3 mg |
| | 120.0 mg |

The compound of the present invention (compound 1), lactose and cornstarch were mixed, kneaded with polyvinylpyrrolidone K30 paste solution and passed through a 20-mesh sieve for granulation. After drying at 50° C. for 2 hours, the granules were passed through a 24-mesh sieve and talc and magnesium stearate were added. The mixture was filled in a hard capsule (No. 4) to give a capsule weighing 120 mg.

Preparative Formulation Example 3

Eye Drop

| Compound of the present invention (compound 2) | 0.05 g |
| --- | --- |
| sodium dihydrogen phosphate | 0.1 g |
| sodium chloride | 0.85 g |
| benzalkonium chloride | 0.005 g |
| sterilized purified water | total amount 100 mL |
| pH | 7.0 |

The compound of the present invention (compound 2), sodium dihydrogen phosphate, sodium chloride and benzalkonium chloride were dissolved in sterilized purified water (ca. 80 mL). The pH was adjusted to 7.0 with hydrochloric acid and sodium hydroxide and sterilized purified water was added to the total amount of 100 mL to give an eye drop.

Using compound 3, compound 4 or compound 5 instead of compound 2, an eye drop is prepared in the same manner.

Preparative Formulation Example 4

Preparation to be Embedded in the Eye compound of the present invention (compound 2) 0.1 g
lactic acid-glycolic acid copolymer (lactic acid:glycolic acid=75:25, molecular weight 5000) 1.0 g The compound of the present invention (compound 2) and lactic acid-glycolic acid copolymer are mechanically mixed and melted at about 80° C. to give a homogeneous mixture. After cooling to allow solidification, the mixture is pulverized in a mortar. The pulverized product (3 mg) was filled in a Teflon tube having an inner diameter of 0.8 mm. The both ends of the Teflon tube filled with the pulverized product was pressed while heating to about 80° C. to give a short rod preparation to be embedded in the eye having a diameter of 0.8 mm and a length of 3 mm.

Using compound 3, compound 4 or compound 5 instead of compound 2, a preparation to be embedded in the eye is prepared in the same manner.

Preparative Formulation Example 5

Tablet

| compound of the present invention (compound 2) | 10 mg |
| --- | --- |
| lactose | 80 mg |
| starch | 17 mg |
| magnesium stearate | 3 mg |
| crystalline cellulose | 10 mg |

Using the above components as materials for one tablet, a tablet is formed by a conventional method. This tablet may be coated as necessary with a sugar coating, a film (e.g., ethylcellulose etc.) to be generally used and the like.

Using compound 3, compound 4 or compound 5 instead of compound 2, a tablet is prepared in the same manner.

Preparative Formulation Example 6

Capsule

| compound of the present invention (compound 2) | 10 mg |
| --- | --- |
| mannitol | 75 mg |
| starch | 17 mg |
| magnesium stearate | 3 mg |

Using the above components as materials for one capsule, granule is produced by a conventional method and filled in a hard capsule. The granule to be filled may be coated as necessary with a film (e.g., ethylcellulose etc.) to be generally used and the like.

Using compound 3, compound 4 or compound 5 instead of compound 2, a capsule is prepared in the same manner.

Preparative Formulation Example 7

Injection

| compound of the present invention (compound 2) | 150 mg |
| --- | --- |
| sodium chloride | 900 mg |
| 1N sodium hydroxide | suitable amount |
| distilled water for injection | total amount 100 mL |

The above components are admixed according to a conventional method to give an injection, from which 0.1 mL is injected into the vitreous body.

Using compound 3, compound 4 or compound 5 instead of compound 2, an injection is prepared in the same manner.

In the following, the pharmacological action of the pharmaceutical agent of the present invention is explained by Examples.

Example 1

In Vitro Experiment (1) Method

Retinal ganglion cells were isolated from an eye ball of a Wistar rat, and cultured in a 48 well plate coated with polylysin (50 µg/mL, Sigma) and merosin (2 µg/mL, GIBCO) at 37° C. under the environment of 5% $CO_2$, 95% air. The number of the cells was about 5000 cells/well. The culture solutions were a culture solution (fetal calf serum-free culture solution) of Neurobasal Medium (GIBCO) supplemented with 50 ng/mL BDNF (human brain-derived neurotrophic factor, Sigma), 50 ng/mL CNTF (rat cilliary neurotrophic factor, Sigma), 5 µM forskolin (Sigma), 1 mM glutamine (Wako) and B27 Supplement (GIBCO; 1 mL/50 mL culture solution), and a culture solution (FCS supplemented culture solution) of the aforementioned fetal calf serum-free culture solution supplemented with 10% fetal calf serum (hereinafter to be also referred to as FCS). After culture for 24 hrs in each culture solution, the group cultured in the FCS supplemented culture solution was divided into 2 groups, and one of them was used as a compound 1 addition group with the addition of 10 µM of compound 1, and the other was used as a compound 1 non-addition group. Similarly, the group cultured in the FCS-free culture solution was divided into a compound 1 addition group and a compound 1 non-addition group. After further culture for 24 hrs, the level of extension of nerve axon of a retinal ganglion cell was observed under an inverted light microscope.

(2) Results

The results are shown in FIG. 1. In FIG. 1, A shows a retinal ganglion cell cultured for 48 hrs in an FCS-supplemented culture solution, B shows a retinal ganglion cell which was cultured in an FCS-supplemented culture solution for 24 hrs, and after addition of 10 µM compound 1, further cultured for 24 hrs, C shows a retinal ganglion cell cultured in an FCS-free culture solution for 48 hrs, and D shows a retinal ganglion cell cultured in an FCS-free culture solution for 24 hrs, and after addition of 10 µM compound 1, further cultured for 24 hrs.

The retinal ganglion cell cultured in an FCS-supplemented culture solution for 48 hrs hardly showed formation of neurite (A). When the retinal ganglion cell was cultured for 24 hrs in an FCS-supplemented culture solution, added with 10 µM compound 1 and further cultured for 24 hrs, the retinal ganglion cell formed a neurite at a high speed (extension of nerve axon), and clearly showed a retinal ganglion cell nerve axon extending action, as compared to compound 1 non-addition group (B).

In a retinal ganglion cell cultured in an FCS-free culture solution from the start of the culture, too, the extension of nerve axon was observed (C). In contrast, when compound 1 was added to an FCS-free culture solution, the extension of nerve axon became remarkable and an action of the compound 1 to promote extension of the nerve axon was confirmed (D).

From the above, it has been found that the compound 1 has an action of extension of nerve axon of a retinal ganglion cell and an action of promotion of extension of axon.

While this Experimental Example discloses only the experimental results using Wister rats, SD rats were also subjected to a similar experiment. As a result, similar axonal extension action and axonal extension promoting action of compound 1 were observed in the retinal ganglion cell.

Example 2

In Vivo Experiment (1) Method

The optic nerve of SD rats weighing 220–280 g was cut under pentobarbital sodium (0.4 mg/kg, i.p.) anesthesia. Separately, the sciatic nerve of the optic nerve-severed rat was taken out in about 3–4 cm and autografted at an end of the optic nerve, which had been cut earlier. The compound 1 dissolved to 120 µmol/L was injected into the vitreous body by 5 µL immediately before cutting the optic nerve, and gelatin pieces (3 mm×3 mm; Spongel, Yamanouchi Pharm.) immersed in a 10 µmol/L solution of compound 1 were embedded around the autograft (compound 1 treatment group). For the non-treatment group, physiological saline was used instead of compound 1 for both the injection into the vitreous body and preparation of the gelatin pieces. During the grafting, attention was paid to avoid damage to the ophthalmic artery, and after grafting, the retinal vascular network was confirmed with a funduscope before breeding under a temperature 23° C.±2, humidity 55±10% environment. The rats were allowed to have a free access to a feed and water. After 6 weeks from the grafting operation, the graft was transversely cut under pentobarbital sodium (0.4 mg/kg, i.p.) anesthesia, and gelatin pieces immersed in 10% GB (p-amidinophenyl p-(6-amidino-2-indolyl)phenyl ether, Sigma, St. Louis, Mo.) were embedded in the cut area of the graft, thereby to retrogradely label retinal ganglion cells. After 48 hrs, the eye ball of the rat was enucleated and a retinal extension sample was prepared according to a conventional method. The images of the retinal extension samples observed under a microscope were directly imported into computer images from the fluorescence microscope and the retrogradedly labeled retinal-ganglion cells were counted using an image analyzing soft (MacSCOP, MITANI CO.). The obtained number of the retrogradedly labeled retinal ganglion cells was taken as a regenerated optic nerve cells. Meanwhile, the optic nerve of the rat free of grafting was cut, gelatin pieces immersed in 10% GB were embedded similarly, and 48 hrs later, the number of the labeled retinal ganglion cells of the retinal extension sample was taken as the number of optic nerve cells of the control.

The ratios (%) of the regenerated cell counts of the non-treatment group and compound 1 treatment group, relative to the optic nerve cell counts of the control, were calculated.

(2) Results

Figure 2:
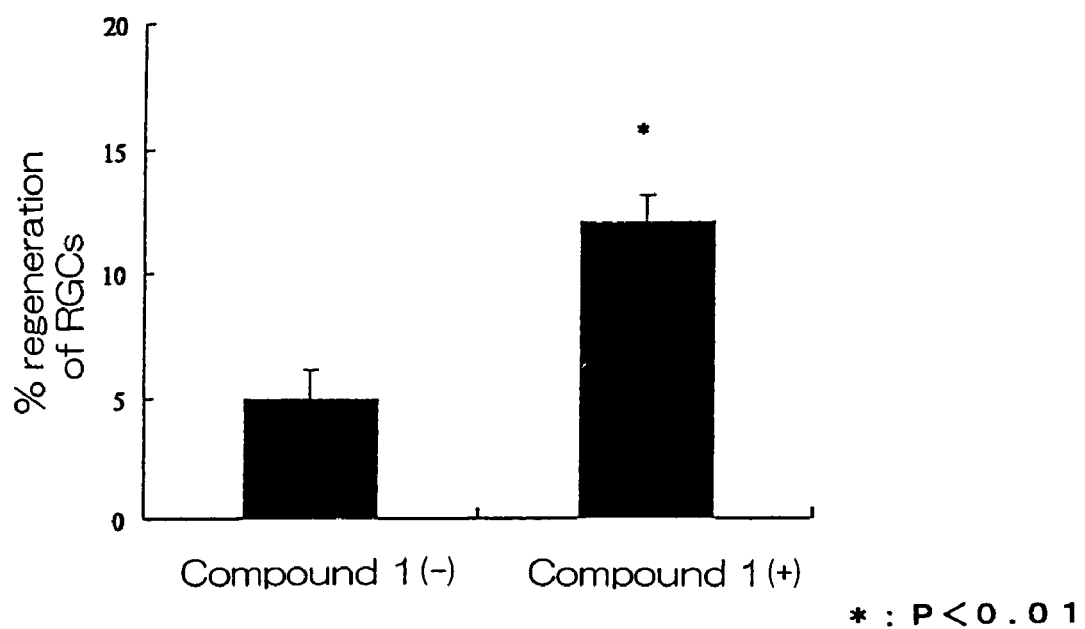
FIG. 2 is a graph showing the measurement results of the level of regeneration of an optic nerve cell in rats, on which the optic nerve was cut off and the sciatic nerve was auto-transplanted, wherein the vertical axis shows the proportion of the regenerated optic nerve cells per 1 mm$^2$ relative to the control group, which was measured both when a Rho kinase inhibitor (compound 1) was and was not added.

The results are shown in FIG. 2. The regenerated optic nerve cell count of the non-treatment group was about 5% of that of the control group. In contrast, the regenerated optic nerve cell count of the compound 1 treatment group was about 12% of the control group and about 2.4 times that of the non-treatment group.

From the above, it has been found that compound 1 has an optic nerve cell regeneration promoting action.

Example 3

In Vitro Experiment (1) Method

Retinal ganglion cells were isolated from an eye ball of a Wistar rat and cultured in a 48 well plate coated with polylysine (50 µg/mL, Sigma) and merosin (2 µg/mL, GIBGO) at 37° C. under the environment of 5% $CO_2$, 95% air. The number of cells was about 5000 cells/well. The culture solution was a culture solution (FCS-free culture solution) of Neurobasal Medium (GIBCO) supplemented with 50 ng/mL BDNF (human brain-derived neurotrophic factor, Sigma), 50 ng/mL CNTF (rat cilliary neurotrophic factor, Sigma), 5 µM forskolin (Sigma), 1 mM glutamine (Wako) and B27 Supplement (GIBCO; 1 mL/50 mL culture solution). After culture for 24 hrs in a culture solution of the aforementioned FCS-free culture solution supplemented with 10% FCS (FCS-supplemented culture solution containing Rho activator) and an FCS-free culture solution, the group cultured in the FCS-free culture solution was divided into 2 groups, and one of them was used as a compound 2 addition group with the addition of 10 µM of compound 2, and the other was used as a compound 2 non-addition group. After further culture for 24 hrs, the level of extension of nerve axon of a retinal ganglion cell was observed under an inverted light microscope. In addition, 1 µM lysophosphatidic acid (LPA), which is a Rho activator, was added to an FCS-free group and axon retraction due to Rho activation was also examined.

(2) Results

Figure 3:
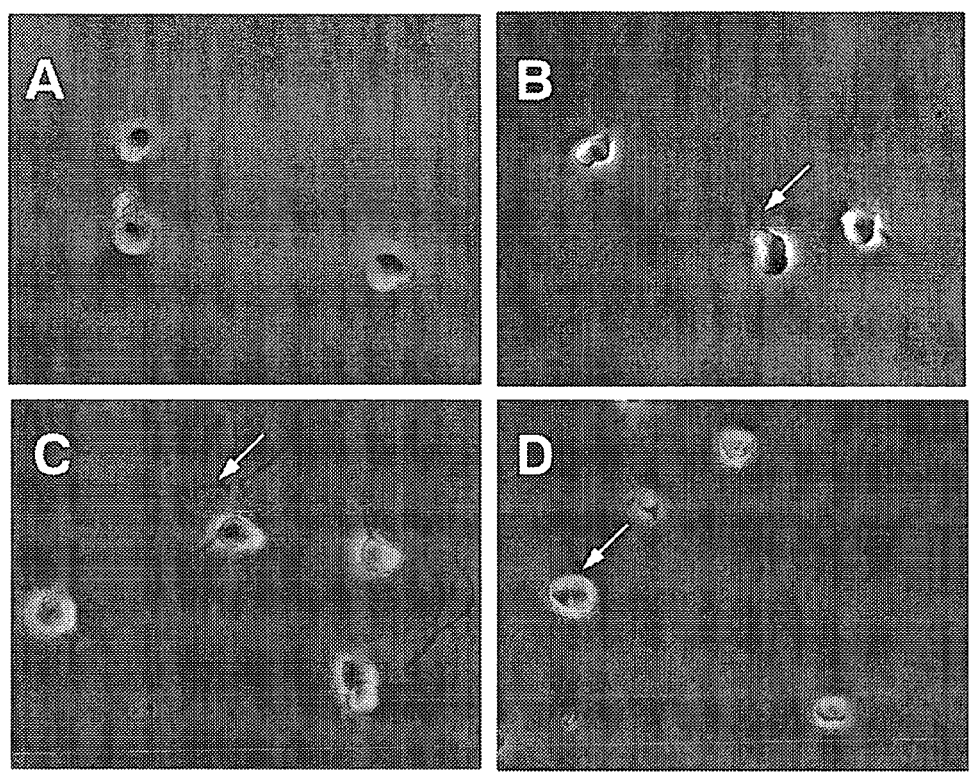
FIG. 3 shows a microscopic image indicating the level of extension of the nerve axon of retinal ganglion cell in the presence or absence of a Rho kinase inhibitor (compound 2), wherein A shows an image of culture in a culture medium with the addition of FCS, B shows an image of culture in a culture medium without the addition of FCS, C shows an image of culture in a medium without the addition of FCS and then with the addition of a Rho kinase inhibitor, and D shows an image of culture in a medium without addition of FCS and then with the addition of LPA, which is a Rho activator.

The results are shown in FIG. 3. In FIG. 3, A shows a retinal ganglion cell cultured for 48 hrs in an FCS-supplemented culture solution, B shows a retinal ganglion cell cultured for 48 hrs in an FCS-free culture solution for 48 hrs, C shows a retinal ganglion cell cultured in an FCS-free culture solution for 24 hrs, and after addition of 10 µM compound 2, further cultured for 24 hrs, and D shows a retinal ganglion cell cultured in an FCS-free culture solution for 44 hrs, and after addition of 1 µM LPA, further cultured for 4 hrs.

The retinal ganglion cell cultured for 48 hrs in an FCS-supplemented culture solution, containing a Rho activator in the early stages of culture, hardly showed formation of neurite (A). A retinal ganglion cell cultured in an FCS-free culture solution from the start of the culture showed a short extension of nerve axon (B). When cultured for 24 hrs in an FCS-free culture solution, added with 10 pM compound 2 and further cultured for 24 hrs, the retinal ganglion cell extended the nerve axon at a high speed, and clearly showed an action of extending the nerve axon of the retinal ganglion cell (C). In the addition group where an FCS-free culture solution supplemented with 1 µM of LPA was used, an axon retraction effect due to the activation of Rho was observed (D).

From the above, it has been found that compound 2 has a nerve axon extending action and a promoting action on extension of nerve axon of a retinal ganglion cell. These actions were suppressed by activation of Rho.

Example 4

In Vivo Experiment (1) Method

The optic nerve of SD rats weighing 220–280 g was cut under pentobarbital sodium (0.4 mg/kg, i.p.) anesthesia. Separately, the sciatic nerve of the optic nerve-severed rat was taken out in about 3–4 cm and autografted at an end of the optic nerve, which had been cut earlier. The compound 2 dissolved to 120 µM was injected into the vitreous body by 5 µL immediately before cutting the optic nerve, and gelatin pieces (3 mm×3 mm; Spongel, Yamanouchi Pharm.) immersed in a 10 µM solution of compound 2 were embedded around the autograft (compound 2 treatment group-1). For compound 2 treatment group-2, the 30 compound 2 dissolved to 1.2 mM was injected into the vitreous body by 5 µL and 100 µM of compound 2 was used around the graft. In the control group, physiological saline was used instead of compound 2. During the grafting, attention was paid to avoid damage to the ophthalmic artery, and after grafting, the retinal vascular network was confirmed with a funduscope before breeding under a temperature 23° C.±2, humidity 55±10% environment. The rats were allowed to have a free access to a feed and water.

Figure 4:
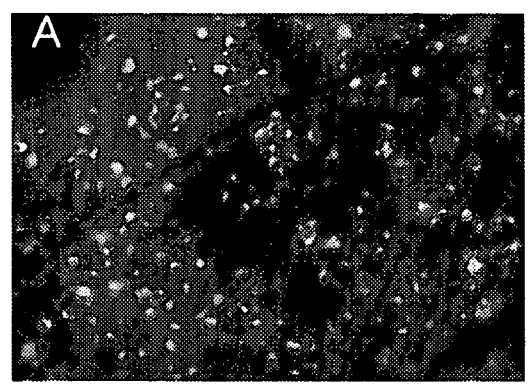
FIG. 4 shows images under microscope (fluorescence microscope) showing the measured results by retrograde labeling of the regenerated optic nerve cell in rats, on which the optic nerve was cut off and the sciatic nerve was auto-transplanted, wherein A shows the labeled optic nerve cell of rats (normal group) free of transplantation, B shows labeled regenerated optic nerve cell in the absence of a Rho kinase inhibitor after cutting off the optic nerve of the rats and auto-transplanting the sciatic nerve (control group), C shows labeled optic nerve cell in the presence of a Rho kinase inhibitor after cutting off the optic nerve of the rats and auto-transplanting the sciatic nerve (compound 2 treatment group-1).
Figure 4:
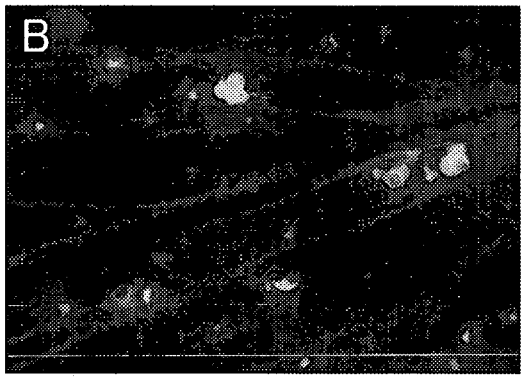
Figure 4:
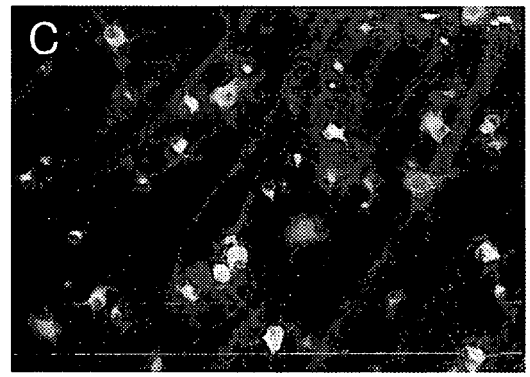

After 6 weeks from the grafting operation, the graft was transversely cut under pentobarbital sodium (0.4 mg/kg, i.p.) anesthesia, and 4-Di-10ASP [4-(4-didecylaminostyryl)-N-methyl-propidium iodide, Sigma, St. Louis, Mo.] crystal (ca. 2 mg) was embedded in the cut area of the graft, thereby to retrogradely label retinal ganglion cells. After 3 days, the eye ball of the rat was enucleated and a retinal extension sample was prepared according to a conventional method. The images of the retinal extension samples observed under a microscope were directly imported into computer images from the fluorescence microscope and the retrogradely labeled retinal ganglion cells were counted using an image analyzing soft (MacSCOP, MITANI CO.)(FIG. 4). The obtained number of the retrogradely labeled retinal ganglion cells was taken as indicating the regenerated optic nerve cells. Meanwhile, the optic nerve of the rat free of grafting was cut, 4-Di-10ASP crystal (ca. 2 mg) was embedded similarly, and the number of the labeled retinal ganglion cells of the retinal extension sample was taken as the number of optic nerve cells of the normal group.

The ratios (%) of the regenerated optic nerve cell counts of the control group, compound 2 treatment group-1 and compound 2 treatment group-2, relative to the optical nerve cell counts of the control, were calculated.

(2) Results

Figure 5:
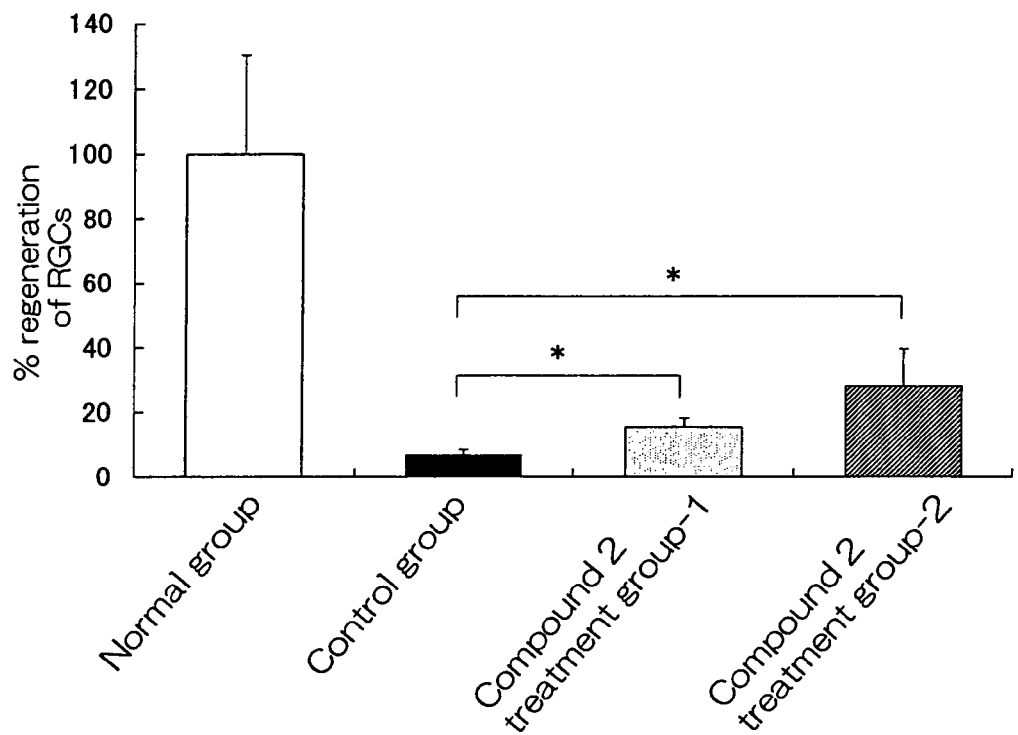
FIG. 5 is a graph showing the measurement results of the level of regeneration of an optic nerve cell in rats, on which the optic nerve was cut off and the sciatic nerve was auto-transplanted, wherein the vertical axis shows the proportion of the regenerated optic nerve cells per 1 mm$^2$ relative to the normal group.

The regenerated optic nerve cell count of the control group was about 7% of the normal group. In contrast, the regenerated optic nerve cell count of the compound 2 treatment group-1 was about 16% of the normal group, and the regenerated optic nerve cell count of the compound 2 treatment group-2 was about 28% of the normal group. They were about 2.3 times and about 4 times that of the control group (FIG. 5).

From the above, it has been found that compound 2 promotes regeneration of the optic nerve cells.

Example 5

In Vitro Experiment (1) Method

In the same manner as in Examples 1 and 3, retinal ganglion cells isolated from the eye ball of 6 to 8-day-old Wistar rats (male-female mixture, SLC) were cultured (cell count: ca. 2000 cells/well). The test compounds (compounds 3–5) were added to the culture solution to the final concentration of 10 µM and respectively used as compound 3 addition group, compound 4 addition group and compound 5 addition group. The control was a test compound non-addition group. The compound 3 (4-[2-(2,3,4,5,6-pentafluorophenyl)acryloyl]cinnamic acid) was synthesized according to the description of Example 8 of JP-A-2000-44513 and used. As compound 4 (ethacrynic acid), one made by Sigma was used and as compound 5 (fasudil hydrochloride), a commercially-available fasudil hydrochloride hydrate injection: "Eril® Injection 30 mg" (produced and sold by Asahi Kasei Corporation) was used.

Using LIVE/DEAD® Viability/Cytotoxicity Kit (L-3224) (Molecular probes) and utilizing the fluorescence characteristics of viable cells by Calcein AM, Calcein AM was uptaken into the retinal ganglion cells and the level of extension of nerve axon of a retinal ganglion cell was observed under a fluorescence microscope. The images of the retinal extension samples observed under a microscope were directly imported into computer images from the fluorescence microscope and the length of the nerve axon was measured using an image analyzing soft (MacSCOP, MITANI CO.). The cells having an axon of not less than 100 μm in length were taken as long neurites cells, the cells having an axon of 21 μm–99 μm were taken as middle neurites cells, and the cells having an axon of not more than 20 μm in length were taken as short neurites cells (no axonal extension). The proportion (%) of the long neurites cells and middle neurites cells relative to the whole cells was calculated for each.

(2) Results

Figure 6:
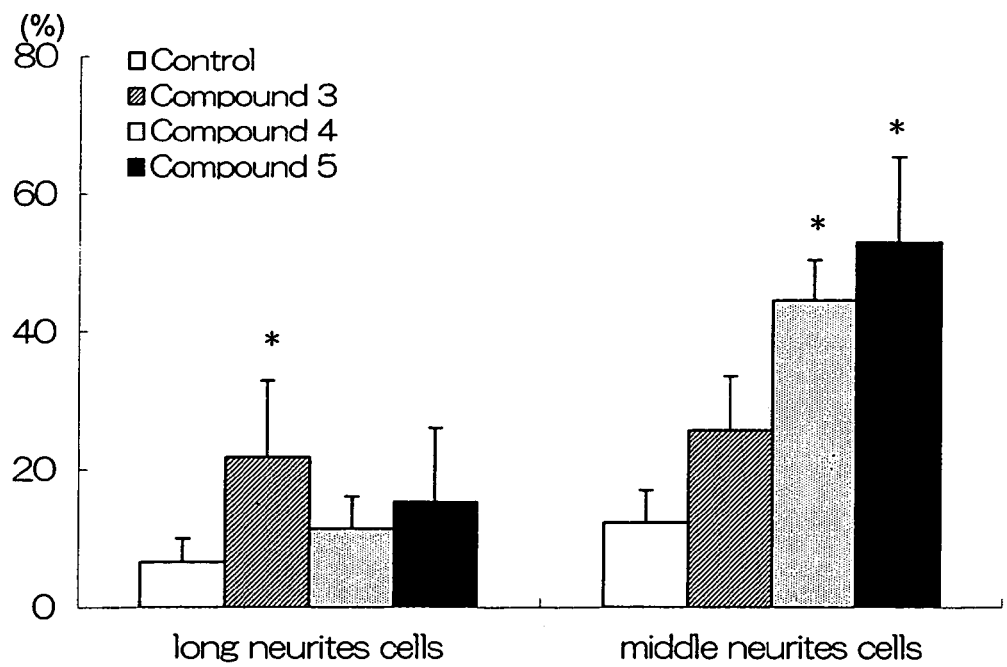
FIG. 6 is a graph showing the influence of various Rho kinase inhibitors (compound 3, compound 4 and compound 5) on extension of axon of a retinal ganglion cell, wherein the vertical axis shows the proportion of axon extended cell count relative to the retinal ganglion cell count. In the Figure, the results with * indicate a significant difference ($p<0.05$) from the control.

The results of the length of the axon of the retinal ganglion cell as measured using an image analyzing soft are shown in FIG. 6.

The long neurites cells and middle neurites cells of the control group (N=3) were 7% and 12%, respectively. In contrast, the long neurites cells and middle neurites cells of the compound 3 addition group (N=3) were 22% and 23%, respectively; the long neurites cells and middle neurites cells of the compound 4 addition group (N=3) were 11% and 45%, respectively; and the long neurites cells and middle neurites cells of the compound 5 addition group (N=3) were 15% and 53%, respectively. It was confirmed that, as compared to the control group, the test compound addition groups increased long neurites cells and the middle neurites cells for all 3 groups. A significant axonal extension promoting action was confirmed (P<0.05) in long neurites cells for the compound 3 addition group and in middle neurites cells for the compound 4 and 5 addition groups, as compared to the control group.

From the above results, the possibility was suggested that in ganglion cells purely isolated from the retina and cultured, a compound having Rho kinase inhibitory activity is involved in the axon regeneration of the retinal ganglion cells.

Reference Example 1

Production of (R)-(+)-N-(1H-pyrrolo[2,3-b]pyridin-4-yl)-4-(1-aminoethyl)benzamide Dihydrochloride 3/2 Hydrate (a) To a solution of (R)-4-(1-benzyloxycarbonylaminoethyl)-benzoic acid (1.2 g) in dichloromethane (15 mL) were added thionyl chloride (0.9 mL) and one drop of dimethylformamide, and the mixture was stirred at room temperature for 2 hrs. After the reaction, the solvent was evaporated under reduced pressure to give (R)-4-(1-benzyloxycarbonylaminoethyl)benzoic acid chloride as crystals. Then, the crystals were dissolved in acetonitrile (10 mL) and added dropwise to a solution of 4-amino-1H-pyrrolo[2,3-b]pyridine (240 mg) and diisopropylethylamine (520 mg) in acetonitrile (10 mL), and the mixture was stirred at room temperature for 8 hrs. The precipitated crystals were collected by filtration and dissolved in methanol (7 mL). Sodium methoxide (60 mg) was added and the mixture was stirred at room temperature for 30 min. After the reaction, the mixture was concentrated under reduced pressure. Water was added to the obtained residue and the mixture was extracted with ethyl acetate. The extract was dried and the solvent was evaporated under reduced pressure. The obtained crystals were washed with ethyl acetate to give (R)-N-(1H-pyrrolo[2,3-b]pyridin-4-yl)-4-(1-benzyloxycarbonylaminoethyl)benzamide (330 mg).

PMR (DMSO-$d_6$/TMS) δ: 1.33–1.40 (3H, m), 4.72–4.78 (1H, m), 4.98–5.04 (2H, m), 6.78–6.82 (1H, m), 7.32–8.16 (13H, m)

(b) To a mixture of (R)-N-(1H-pyrrolo[2,3-b]pyridin-4-yl)-4-(1-benzyloxycarbonylaminoethyl)benzamide (200 mg), 15% hydrochloric acid-methanol (1 mL) and methanol (6 mL) was added 10% palladium hydroxide carbon (80 mg), and the mixture was stirred under a hydrogen stream at 40° C. for 1 hr. After the reaction, the catalyst was filtered off and the residue was concentrated under reduced pressure. The obtained crystals were recrystallized from methanol-ether to give (R)-(+)-N-(1H-pyrrolo[2,3-b]pyridin-4-yl)-4-(1-aminoethyl)benzamide dihydrochloride 3/2 hydrate (120 mg), melting point: 286° C. (decomposition).

$[\alpha]_D$=+6.1° (methanol, c=1) PMR (DMSO-$d_6$/TMS)δ: 1.54 (3H, d, J=6.8 Hz), 4.50–4.54 (1H, m), 7.11 (1H, br), 7.55 (1H, br), 7.70 (2H, d, J=8.3 Hz), 8.02–8.06 (3H, m), 8.33 (1H, br), 8.62 (3H, br), 10.99 (1H, br)

Reference Example 2

Production of (R)-(+)-N-(1H-pyrrolo[2,3-b]pyridin-4-yl)-4-(1-aminoethyl)benzamide Monohydrochloride (a) (R)-(+)-N-(1H-pyrrolo[2,3-b]pyridin-4-yl)-4-(1-aminoethyl)benzamide dihydrochloride 3/2 hydrate (8.5 g) obtained in Reference Example 1 was dissolved in water (50 mL) and 1N-NaOH aqueous solution was added dropwise while stirring under ice-cooling. The precipitated crystals were collected by filtration and dried (warm air: 60° C., 10 hrs) to give a free base form (6.2 g).

mp. 210–212° C. EA: calcd. for $C_{16}H_{16}N_4O$: C, 68.55; H, 5.75; N, 19.99. found C, 68.58; H, 5.70; N, 19.81. $^1$H-NMR (DMSO-$d_6$)δ: 1.29 (3H, d, J=8.0 Hz), 1.88 (2H, bs), 4.09 (1H, m), 6.80 (1H, s), 7.33 (1H, s), 7.53 (2H, d, J=7.8 Hz), 7.70 (1H, d, J=7.8 Hz), 7.92 (2H, d, J=7.8 Hz), 8.14 (1H, d, J=7.8 Hz), 10.26 (1H, bs), 11.57 (1H, bs) $[\alpha]_D$=+14.7° (methanol, c=0.5)

(b) To the free base form (2.8 g) obtained in the above-mentioned (a) was added ethanol (5 mL), and 1N hydrochloric acid (10 mL) was added while heating to 60° C. After dissolution, the mixture was filtered while it was hot and stirred at room temperature for 2 hrs and in an ice-salt bath for 1.5 hrs. The precipitated crystals were collected by filtration, dried (warm air: 60° C., 10 hrs) and H$_2$O-EtOH (2/1) (20 mL) was added. After dissolving under reflux, the mixture was filtered while it was hot and stirred at room temperature for 2 hrs and in an ice-salt bath for 1.5 hrs. Thereafter, the crystals were collected by filtration and dried (warm air: 60° C., 24 hrs) to give (R)-(+)-N-(1H-pyrrolo[2,3-b]pyridin-4-yl)-4-(1-aminoethyl)benzamide onohydrochloride (2.4 g).

mp. 298° C. (decomposition) EA: calcd. for $C_{16}H_{16}N_4O.1HCl$ C, 60.66; H, 5.41; N, 17.69 found C, 60.56; H, 5.32; N; 17.62 $^1$H-NMR(DMSO-$d_6$)δ: 1.58 (3H, d, J=8.0 Hz), 4.51 (1H, m), 6.80 (1H, s), 7.35 (1H, s), 7.70 (3H, m), 8.05 (2H, d, J=7.8 Hz), 8.15 (1H, d, J=7.8 Hz), 8.68 (3H, bs), 10.41 (1H, bs), 11.60 (1H, bs) $[\alpha]_D$=+8.2° (methanol, c=1.0)

INDUSTRIAL FIELD OF UTILIZATION

Since compounds 1 to 5 have axon of the retinal ganglion cell extending action and optic nerve cell regenerating action, a compound having Rho kinase inhibitory activity is considered to improve visual function disorders caused by damage, degeneration and the like of the retinal nerve and the optic nerve. Accordingly, a compound having Rho kinase inhibitory activity is considered to be effective for the improvement of visual function in a visual disorder caused by damage due to retinal inflammation and the like (retinal neuropathy, retinal vascular occlusion, periphlebitis retinae, Eales' disease, ischemic ophthalmopathy, retinal arteriolar microaneurysm, retinopathy caused by hypertension, renal disease and blood disease, diabetic retinopathy, retinal dystrophy, macular dystrophy, chorioretinopathy, macular degeneration, macular edema, retinal pigment epithelium detachment, degenerative retinoschisis, retinoblastoma, retinal pigment epithelioma etc.) and the like; improvement of visual function in a visual disorder caused by degeneration, damage of the optic nerve (optic neuritis, capillary angioma of optic disc, ischemic optic neuropathy, defects of retinal nerve fibers layer, retinal optic atrophy, neurotmesis of optic nerve, traumatic optic neuropathy, choked disc, coloboma of optic disc, optic nerve hypoplasia, toxic optic atrophy etc.); improvement of visual function in a visual disorder due to optic atrophy, degeneration and the like caused by elevated intraocular pressure (glaucoma etc.) and the like; and further, proliferation and functional maintenance of visual cells including retinal ganglion cells in retinal transplantation as well as regeneration of optic nerve in optic nerve transplantation.

This application is based on patent application Nos. 2001-113329 and 2001-308010 filed in Japan, the contents of which are all hereby incorporated by reference.

The invention claimed is:

1. A method of promoting extension of axon of a retinal ganglion cell, which comprises administering an effective amount of a compound having Rho kinase inhibitory activity to a patient wherein the compound having Rho kinase inhibitory activity is an amide compound represented by the formula (I)

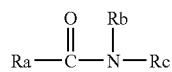

(I)

wherein

Ra is a group of the formula

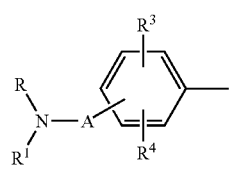

(b)

in the formula (b),

R is hydrogen, alkyl, or cycloalkyl, cycloalkylalkyl, phenyl or aralkyl, which optionally has a substituent on the ring, or a group of the formula

(d)

wherein $R^6$ is hydrogen, alkyl or formula:—$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

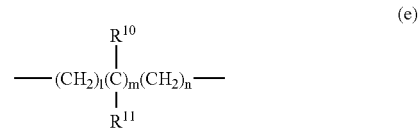

(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and 1, m and n are each 0 or an integer of 1–3, Rb is a hydrogen, an alkyl, an aralkyl, an aminoalkyl or a mono- or dialkylaminoalkyl; and Rc is an optionally substituted 6-membered ring containing one nitrogen atom, an isomer thereof and/or a pharmaceutically acceptable acid addition salt thereof.

2. A method of promoting extension of axon of a retinal ganglion cell, which comprises administering an effective amount of a compound having Rho kinase inhibitory activity to a patient wherein the compound having Rho kinase inhibitory activity is an amide compound represented by the formula (I')

(I')

wherein
Ra' is a group of the formula

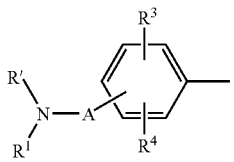
(b')

wherein
Ra' is hydrogen, alkyl, or cycloalkyl, cycloalkylalkyl, phenyl or aralkyl, which optionally has a substituent on the ring, $R^1$ is hydrogen, alkyl. or cycloalkyl, cycloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

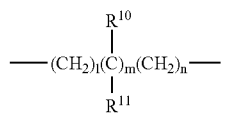
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and 1, m and n are each 0 or an integer of 1–3, Rb is a hydrogen, an alkyl, an aralkyl, an aminoalkyl or a mono- or dialkylaminoalkyl; and Rc is an optionally substituted 6-membered ring containing one nitrogen atom, an isomer thereof and/or a pharmaceutically acceptable acid addition salt thereof.

3. The method of claim 1 wherein the compound having Rho kinase inhibitory activity is (R)-(+)-N-(1H-pyrrolo[2,3-b]pyridin-4-yl)-4-(1-aminoethyl)benzamide or a pharmaceutically acceptable acid addition salt thereof.

4. The method of claim 1 wherein the compound having Rho kinase inhibitory activity is (R)-(+)-N-(1H-pyrrolo[2,3-b]pyridin-4-yl)-4-(1-aminoethyl)benzamide monohydrochloride.

5. A method of promoting regeneration of an optic nerve cell, which comprises administering an effective amount of a compound having Rho kinase inhibitory activity to a patient wherein the compound having Rho kinase inhibitory activity is an amide compound represented by the formula (I)

(I)

wherein
Ra is a group of the formula

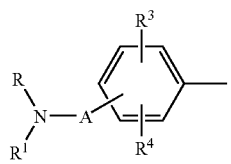
(b)

in the formula (b),
R is hydrogen, alkyl, or cycloalkyl. cycloalkylalkyl, phenyl or aralkyl, which optionally has a substituent on the ring, or a group of the formula

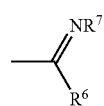
(d)

wherein $R^6$ is hydrogen, alkyl or formula:—$NR^8R^9$ wherein $R^8$ and $R^9$ are the same or different and each is hydrogen, alkyl, aralkyl or phenyl, $R^7$ is hydrogen, alkyl, aralkyl, phenyl, nitro or cyano, or $R^6$ and $R^7$ in combination show a group forming a heterocycle optionally further having, in the ring, oxygen atom, sulfur atom or optionally substituted nitrogen atom, $R^1$ is hydrogen, alkyl, or cycloalkyl, cycloalkylalkyl, phenyl or aralkyl, which optionally has a substituent on the ring, or R and $R^1$ in combination form, together with the adjacent nitrogen atom, a group forming a heterocycle optionally further having, in the ring, oxygen atom, sulfur atom or optionally substituted nitrogen atom, $R^3$ and $R^4$ are the same or different and each is hydrogen, alkyl, aralkyl, halogen, nitro, amino, alkylamino, acylamino. hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

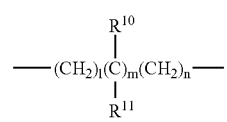
(e)

wherein $R^{10}$ and $R^{11}$ are the same or different and each is hydrogen, alkyl, haloalkyl, aralkyl, hydroxyalkyl, carboxy or alkoxycarbonyl, or $R^{10}$ and $R^{11}$ show a group which forms cycloalkyl in combination and 1, m and n are each 0 or an integer of 1–3, Rb is a hydrogen, an alkyl, an aralkyl, an aminoalkyl or a mono- or dialkylaminoalkyl; and Rc is an optionally substituted 6-membered ring containing one nitrogen atom, an isomer thereof and/or a pharmaceutically acceptable acid addition salt thereof.

6. A method of promoting regeneration of an optic nerve cell, which comprises administering an effective amount of a compound having Rho kinase inhibitory activity to a patient wherein the compound having Rho kinase inhibitory activity is an amide compound represented by the formula (I')

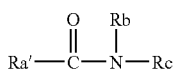 (I')

wherein
Ra' is a group of the formula

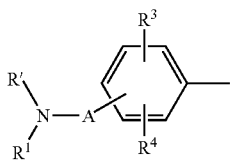 (b')

wherein
R' is hydrogen, alkyl, or cycloalkyl, cycloalkylalkyl, phenyl or aralkyl, which optionally has a substituent on the ring, $R^1$ is hydrogen, alkyl, or cycloalkyl, cycloalkylalkyl, phenyl or aralkyl, which optionally has a substituent on the ring, or R' and $R^1$ in combination form, together with the adjacent nitrogen atom, a group forming a heterocycle optionally further having, in the ring, oxygen atom, sulfur atom or optionally substituted nitrogen atom, $R^3$ and $R^4$ are the same or different and each is hydrogen, alkyl, aralkyl, halogen, nitro, amino, alkylamino, acylamino, hydroxy, alkoxy, aralkyloxy, cyano, acyl, mercapto, alkylthio, aralkylthio, carboxy, alkoxycarbonyl, carbamoyl, mono- or dialkylcarbamoyl or azide, and A is a group of the formula

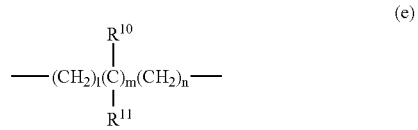 (e)

wherein $R^{10}$ and $R^{11}$ are the same or different and each is hydrogen, alkyl, haloalkyl, aralky, hydroxyalkyl, carboxy or alkoxycarbonyl, or $R^{10}$ and $R^{11}$ show a group which forms cycloalkyl in combination and 1, m and n are each 0 or an integer of 1–3, Rb is a hydrogen, an alkyl, an aralkyl, an aminoalkyl or a mono- or dialkylaminoalkyl; and Rc is an optionally substituted 6-membered ring containing one nitrogen atom, an isomer thereof and/or a pharmaceutically acceptable acid addition salt thereof.

7. The method of claim 5, wherein the compound having Rho kinase inhibitory activity is (R)-(+)-N-(1H-pyrrolo[2,3-b]pyridin-4-yl)-4-(1-aminoethyl)benzamide or a pharmaceutically acceptable acid addition salt thereof.

8. The method of claim 5, wherein the compound having Rho kinase inhibitory activity is (R)-(+)-N-(1H-pyrrolo[2,3-b]pyridin-4-yl)-4-(1-aminoethyl)benzamide monohydrochloride.

* * * * *